(12) United States Patent
Nishiguchi et al.

(10) Patent No.: US 7,514,379 B2
(45) Date of Patent: Apr. 7, 2009

(54) CURABLE POLYVINYL BENZYL COMPOUND AND PROCESS FOR PRODUCING THE SAME

(75) Inventors: Shouji Nishiguchi, Isesaki (JP); Tatsuhiro Ikeya, Isesaki (JP); Haruo Yoshida, Machida (JP); Jyouji Shibata, Honjou (JP); Hirotaka Kofune, Isesaki (JP)

(73) Assignee: Showa Highpolymer Co., Ltd., Tokyo (JP)

( * ) Notice: Subject to any disclaimer, the term of this patent is extended or adjusted under 35 U.S.C. 154(b) by 486 days.

(21) Appl. No.: 10/954,214

(22) Filed: Oct. 1, 2004

(65) Prior Publication Data

US 2005/0176909 A1 Aug. 11, 2005

Related U.S. Application Data

(63) Continuation-in-part of application No. 10/474,453, filed as application No. PCT/JP02/02851 on Mar. 25, 2002, now abandoned.

(30) Foreign Application Priority Data

Apr. 9, 2001 (JP) ............................. 2001-110125

(51) Int. Cl.
  B32B 27/30 (2006.01)
  B32B 3/00 (2006.01)
  B32B 15/08 (2006.01)
  B32B 15/04 (2006.01)
(52) U.S. Cl. ...................... 442/173; 428/209; 428/416; 428/444
(58) Field of Classification Search ................. 442/173; 428/35.8, 148, 164, 209, 416, 444
See application file for complete search history.

(56) References Cited

U.S. PATENT DOCUMENTS

2004/0106758 A1* 6/2004 Nishiguchi et al. ........ 526/317.1

OTHER PUBLICATIONS

G. Klarner, J.I. Lee, V.Y. Lee, E. Chan, J.P. Chen, A. Nelson, D. Markiewicz, R. Siemens, J.C. Scoot, and R.D. Miller; Cross-linkable Polymers Based on Dialkylfluorenes, Chem. Mater. 1999, vol. 11, 1800-1805.
Klarner, G. et al., "Cross-linkable Polymers Based on Dialkylfluorenes", Chem. Mater. 1999, vol. 11, pp. 1800 to 1805.
G. Kläner, J.-I. Lee, V.Y. Lee, E. Chan, J.-P. Chen, A. Nelson, D. Markiewicz, R. Siemens, J.C. Scott, and R. D. Miller; Cross-linkable Polymers Based on Dialkylfluorenes; Chem. Mater. 1999, vol. 11, No. 7, 1800-1805.

* cited by examiner

*Primary Examiner*—Lynda Salvatore
(74) *Attorney, Agent, or Firm*—Sughrue Mion, PLLC

(57) ABSTRACT

A curable polyvinyl benzyl compound represented by the following general formula (1):

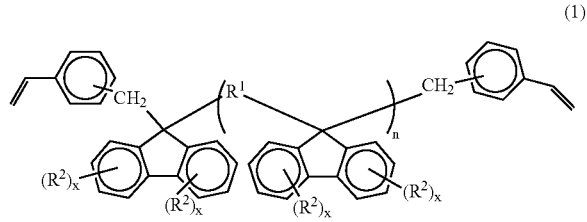

(1)

wherein $R^1$ represents a $C_{2\text{-}20}$ organic group, $R^2$ represents a hydrogen atom, etc., x is an integer of 0 to 4, and n is an integer of 0 to 2. The compound is obtained by reacting a fluorene compound with a vinylbenzyl halide in the presence of an alkali.

11 Claims, 13 Drawing Sheets

CURABLE POLYVINYL BENZYL COMPOUND AND PROCESS FOR PRODUCING THE SAME

CROSS REFERENCE TO RELATED APPLICATIONS

This application is a Continuation-In-Part of U.S. application Ser. No. 10/474,453 filed Oct. 8, 2003 now abandoned, which is the National Stage of PCT/JP02/02851 filed on Mar. 25, 2002.

TECHNICAL FIELD

The present invention relates to a compound which provides a cured product having high heat resistance, low water absorption and excellent dielectric properties which are required for organic insulating materials for use in electronic equipment such as communication equipment and to a process for producing the same. More specifically, the present invention relates to a curable polyvinyl benzyl compound obtained by reacting a fluorene compound with a vinylbenzyl halide, a process for producing the same, and a curable resin composition and a cured resin obtained by using the same. Further, the present invention relates to a substrate, a prepreg and a metal foil having a resin, all of which have excellent dielectric properties at a high-frequency range, in particular, a low dielectric dissipation factor, and high heat resistance.

BACKGROUND ART

Along with recent progress in electronic technology, materials having a low dielectric constant and a low dielectric dissipation factor are now in demand as materials of parts for use in computers and mobile communication equipment. To satisfy this demand, various materials are being developed. The materials include, for example, polybenzocyclobutene (R. A. Kirchhoff et al., Macromol. Symp. 54/55, 531 (1992)), fluorinated polybiphenylene ether (JP 10-74751 A), polyphenylene compound having a heterocyclic side chain (JP 9-278879 A), polyfumarate (JP 9-208697 A), polynorbornene (JP 5-214079 A), polyquinoxaline (JP 2705799 B), fluorinated polyquinoline (JP 6-500591 A), side chain allyl group-substituted polyphenylene ether (JP 64-69628 A, JP 4-183707 A, and JP 6-207096 A), and polyphenylene ether whose terminal is blocked with an allyl group or a propargyl group (JP 7-51625 B).

However, the above materials proposed in the prior art have various problems such as a low crosslinking density and a large linear expansion coefficient; low chemical resistance; poor tenacity; a large number of complicated steps required for the production of a resin from raw materials; and the need for a special solvent for shaping. Therefore, they have not been put to practical use yet.

The inventors of the present invention have proposed a vinylbenzyl ether compound which has low water absorption over a wide temperature range and a wide frequency range, a low dielectric constant and a low dielectric dissipation factor and satisfies the current strict requirements for electronic materials (JP 9-31006 A). This vinylbenzyl ether compound can be synthesized by reacting an aromatic compound having a hydroxyl group with a vinylbenzyl halide in a polar solvent in the presence of an alkali, or in a water/organic solvent mixed solution in the presence of a phase-transfer catalyst.

However, the requirements for dielectric properties of electronic materials are becoming more and more demanding. Next-generation communication devices have begun to appear, which require, in particular, a low dielectric dissipation factor, which cannot be satisfied even by the above vinylbenzyl ether compound.

It is therefore an object of the present invention to provide a polyvinyl benzyl compound which provides a cured product having high heat resistance, low water absorption, a low dielectric constant and a low dielectric dissipation factor, a process for producing the same, a curable resin composition comprising the same, and a cured resin obtained by curing said composition.

It is another object of the present invention to provide a substrate, prepreg and metal foil having a resin all of which have excellent dielectric properties over a high frequency range, in particular, a low dielectric dissipation factor, and high heat resistance.

DISCLOSURE OF THE INVENTION

The invention according to claim 1 relates to a curable polyvinyl benzyl compound represented by the following general formula 1:

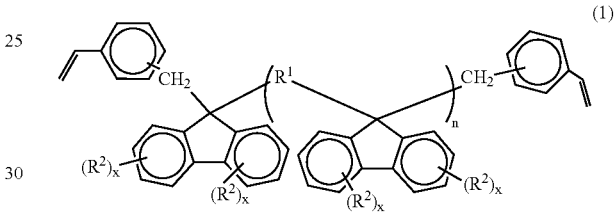

(wherein $R^1$ is a divalent organic group having 2 to 20 carbon atoms, $R^2$ is at least one organic group selected from the group consisting of a hydrogen atom, a halogen atom, an alkyl group, an alkoxy group and a thioalkoxy group having 1 to 5 carbon atoms, which may be the same or different, and an aryl group, where x is an integer of 0 to 4, and n is an integer of 0 to 20).

The invention according to claim 2 relates to a process for producing a curable polyvinyl benzyl compound according to claim 1, characterized by reacting one fluorene compound or two or more fluorene compounds represented by the following general formula 2 and a vinylbenzyl halide in the presence of an alkali:

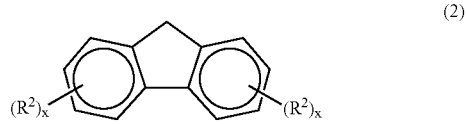

(wherein $R^2$ is at least one organic group selected from a group consisting of a hydrogen atom, a halogen atom, an alkyl group, an alkoxy group and a thioalkoxy group having 1 to 5 carbon atoms, which may be the same or different, and an aryl group, where x is an integer of 0 to 4).

The invention according to claim 3 relates to a process for producing a curable polyvinyl benzyl compound according to claim 1, characterized by reacting one fluorene compound or two or more fluorene compounds represented by the following general formula 2, a vinylbenzyl halide and a dihalomethyl compound having 2 to 20 carbon atoms in the presence of an alkali:

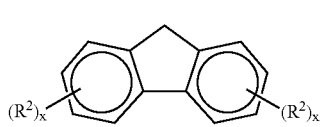 (2)

(wherein $R^2$ is at least one organic group selected from the group consisting of a hydrogen atom, a halogen atom, an alkyl group, an alkoxy group and a thioalkoxy group having 1 to 5 carbon atoms, which may be the same or different, and an aryl group, where x is an integer of 0 to 4).

The invention according to claim 4 relates to the process for producing a curable polyvinyl benzyl compound according to claim 2 or 3, in which vinylbenzyl halide is at least one selected from the group consisting of m-vinylbenzyl chloride and p-vinylbenzyl chloride.

The invention according to claim 5 relates to the process for producing a curable polyvinyl benzyl compound according to claim 3, in which an equivalent ratio of a halomethyl group of the vinylbenzyl halide to the halomethyl group of the dihalomethyl compound having 2 to 20 carbon atoms is 1.0/0 to 0.1/0.9.

The invention according to claim 6 relates to the process for producing a curable polyvinyl benzyl compound according to any one of claims 2 to 5, in which the reaction is carried out in the presence of an aprotic polar solvent and/or a phase-transfer catalyst.

The invention relates to a curable resin composition prepared by mixing a curable polyvinyl benzyl compound with a monomer, an oligomer and/or a polymer which is copolymerizable with said compound.

The invention relates to a cured resin obtained by curing a curable polyvinyl benzyl compound.

The invention relates to a cured resin obtained by curing a curable resin composition.

The invention relates to a high-frequency substrate obtained by curing a curable polyvinyl benzyl compound.

The invention relates to a high-frequency substrate obtained by curing a curable resin composition.

The invention relates to a prepreg obtained by impregnating a curable resin composition with a fiber material.

The invention relates to a high-frequency substrate obtained by heating and pressurizing either a single prepreg or a laminate of the prepregs.

The invention relates to a metal-lined high-frequency substrate obtained by placing a metal foil onto either or single prepreg or a laminate of the prepregs, through heating and pressurizing.

The invention relates to a metal foil having a resin obtained by applying a curable resin composition to a metal foil to be integrated.

The invention relates to a multi-layer laminate substrate characterized by including a curable resin composition applied to a conductive layer, which is polymerized and cured, and a conductive layer formed on a cured product.

The invention relates to a curable vinylbenzyl compound represented by the following general formula 3:

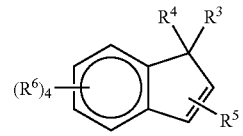 (3)

(wherein, $R^3$, $R^4$, and $R^5$ each represent a group selected from the group consisting of a vinylbenzyl group, a hydrogen atom, an alkyl group, alkoxy group, and thioalkoxy group each having 1 to 5 carbon atoms, which may be the same or different, and an aryl group; at least one of $R^3$, $R^4$, and $R^5$ is a vinylbenzyl group; and $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

The invention relates to a curable vinylbenzyl compound represented by the following general formula 4:

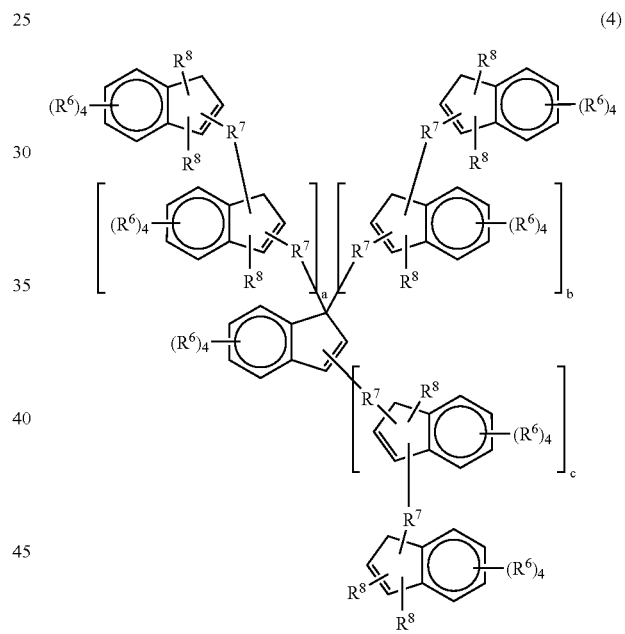 (4)

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group; $R^7$ represents a divalent organic group having 2 to 20 carbon atoms; $R^8$ represents a group selected from the group consisting of a vinylbenzyl group, a hydrogen atom, an alkyl group, alkoxy group, and thioalkoxy group each having 1 to 5 carbon atoms, which may be the same or different, and an aryl group; at least one $R^8$ is a vinylbenzyl group; and a, b, and c each represent an integer of 0 to 20).

The invention relates to a curable vinylbenzyl compound obtained by reacting at least one indene compound represented by the following general formula 5, a fluorene compound, a vinylbenzyl halide, and a dihalomethyl compound having 2 to 20 carbon atoms in the presence of an alkali:

(wherein, R⁶ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

The invention relates to a process for producing the curable vinylbenzyl compound according to the seventeenth aspect of the present invention, including reacting at least one indene compound represented by the following general formula 5 and a vinylbenzyl halide in the presence of an alkali:

(wherein, a definition of $R^6$ is the same as that described above).

The invention relates to a process for producing the curable vinylbenzyl compound including reacting at least one indene compound represented by the following general formula 5, a vinylbenzyl halide, and a dihalomethyl compound having 2 to 20 carbon atoms in the presence of an alkali:

(wherein, a definition of $R^6$ is the same as that described above).

The invention relates to a process for producing a curable vinylbenzyl compound, in which the vinylbenzyl halide is at least one of m-vinylbenzyl chloride and p-vinylbenzyl chloride.

The invention relates to a process for producing a curable vinylbenzyl compound in which an equivalent ratio of a halomethyl group of the vinylbenzyl halide to a halomethyl group of the dihalomethyl compound having 2 to 20 carbon atoms is adjusted to 0.9:0.1 to 0.1:0.9 for a reaction.

The invention relates to a process for producing a curable vinylbenzyl compound, in which the reaction is carried out in the presence of an alkali and in the presence of at least one of an aprotic polar solvent and a phase-transfer catalyst.

The invention relates to a curable resin composition prepared by mixing the curable vinylbenzyl compound with a compound which is copolymerizable with the curable vinylbenzyl compound.

The invention relates to a cured resin obtained by curing the curable vinylbenzyl compound.

The invention relates to a cured resin obtained by curing the curable resin composition.

The invention relates to a high-frequency substrate obtained by polymerizing and curing a polymerizable composition, in which the polymerizable composition contains a fluorene compound having at least one polymerizable unsaturated group in a molecule (except for a case where all of the polymerizable unsaturated groups are vinylbenzyl groups).

The invention relates to a high-frequency substrate, in which the fluorene compound contains one of: at least one of an allyl group and a propargyl group as a polymerizable unsaturated group; and at least one polymerizable unsaturated group and a vinylbenzyl group.

The invention relates to a high-frequency substrate obtained by polymerizing and curing a polymerizable composition, in which the polymerizable composition contains an indene compound having at least one polymerizable unsaturated group in a molecule.

The invention relates to a high-frequency substrate in which the polymerizable unsaturated group is at least one group selected from a vinylbenzyl group, an allyl group, and a propargyl group.

The invention relates to a high-frequency substrate obtained by polymerizing and curing a polymerizable composition, in which the polymerizable composition contains a fluorene compound having at least one polymerizable unsaturated group in a molecule and an indene compound having at least one polymerizable unsaturated group in a molecule.

The invention relates to a high-frequency substrate in which: the fluorene compound is at least one compound represented by the following general formula 6; and the polymerizable composition is a compound obtained by reacting the fluorene compound, a halogen compound having at least one polymerizable unsaturated group selected from the group consisting of a vinylbenzyl halide, an allyl halide, and a propargyl halide, and a dihalomethyl compound having 2 to 20 carbon atoms in the presence of an alkali:

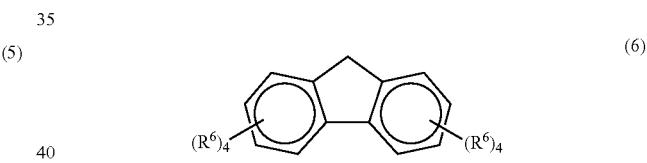

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

The invention relates to a high-frequency substrate in which: the indene compound is at least one compound represented by the following general formula 5; and the polymerizable composition contains a compound obtained by reacting the indene compound, a halogen compound having at least one polymerizable unsaturated group selected from the group consisting of a vinylbenzyl halide, an allyl halide, and a propargyl halide, and a dihalomethyl compound having 2 to 20 carbon atoms in the presence of an alkali:

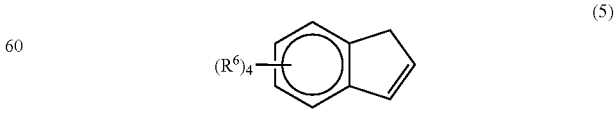

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

The invention relates to a high-frequency substrate in which: the fluorene compound is at least one compound represented by the following general formula 6; the indene compound is at least one compound represented by the following general formula 5; and the polymerizable composition is a compound obtained by reacting the fluorene compound, the indene compound, a halogen compound having at least one polymerizable unsaturated group selected from the group consisting of a vinylbenzyl halide, an allyl halide, and a propargyl halide, and a dihalomethyl compound having 2 to 20 carbon atoms in the presence of an alkali.

The invention relates to a high-frequency substrate, in which an equivalent ratio of a halomethyl group of the halogen compound having a polymerizable unsaturated group to a halomethyl group of the dihalomethyl compound having 2 to 20 carbon atoms is 0.9/0.1 to 0.1/0.9.

The invention relates to a high-frequency substrate, in which the polymerizable composition is a composition prepared by mixing a fluorene compound having at least one polymerizable unsaturated group in a molecule and a compound which is copolymerizable with the fluorene compound.

The invention relates to a high-frequency substrate, in which the polymerizable composition is a composition prepared by mixing an indene compound having at least one polymerizable unsaturated group in a molecule and a compound which is copolymerizable with the indene compound.

The invention relates to a prepreg obtained by impregnating a fiber material with the polymerizable composition.

The invention relates to a prepreg, in which the fiber material is a glass cloth.

The invention relates to a high-frequency substrate obtained by heating and pressurizing one of a single prepreg and a prepreg laminate.

The invention relates to a metal-lined high-frequency substrate obtained by placing a metal foil onto one of a single prepreg and a prepreg laminate, and heating and pressurizing the whole.

The invention relates to a metal foil having a resin obtained by applying the polymerizable composition to a metal foil and integrating the polymerizable composition and the metal foil.

The invention relates to a multi-layer laminate substrate including: a cured product prepared by applying the polymerizable composition to a conductive layer, and polymerizing and curing the composition; and a conductive layer provided on the cured product.

DETAILED DESCRIPTION OF THE INVENTION

The present invention will be described in detail hereinafter.

A first curable vinylbenzyl compound of the present invention is obtained by reacting one fluorene compound or two or more fluorene compounds represented by the above general formula 2 with a vinylbenzyl halide and optionally a dihalomethyl compound having 2 to 20 carbon atoms in the presence of an alkali. The reaction can be carried out in accordance with conditions for a known vinylbenzylation reaction. The vinylbenzylation reaction is described, for example, by L. J. Mathias et al. in J. Polym. Sci., Part B; 36, 2869 (1998) and J. Polym. Sci., Part A; 35, 587 (1997), and by C. J. Kelly et al. in J. Chem. Res. (S), 446 (1997).

Examples of the fluorene compound used in the present invention include fluorene compounds whose fluorene and aromatic ring parts may be substituted by an alkyl group, alkoxy group, thioalkoxy group or aryl group as represented by the above general formula 2. They may be used alone or in combination of two or more compounds.

Examples of the vinylbenzyl halide used in the present invention include m-vinylbenzyl chloride, p-vinylbenzyl chloride, m-vinylbenzyl bromide and p-vinylbenzyl bromide. They may be used alone or in combination of two or more compounds. Of these, m-vinylbenzyl chloride and p-vinylbenzyl chloride are preferred.

The dihalomethyl compound used in the present invention is a compound having two —$CH_2X$ (where X is a halogen atom) groups in the molecule and 2 to 20 carbon atoms, preferably 2 to 16 carbon atoms. Examples of the dihalomethyl compound include halogenated alkyls such as 1,2-dichloroethane, 1,2-dibromoethane, 1,3-dichloropropane, 1,3-dibromopropane, 1,4-dichlorobutane and 1,4-dibromobutane, and compounds such as o-xylylene dichloride, m-xylylene dibromide, p-xylylene dibromide, 4,4'-bis(chloromethyl)biphenyl, 4,4'-bis(chloromethyl)diphenyl ether, 4,4'-bis(chloromethyl)diphenyl sulfide, 2,6-bis(bromomethyl)naphthalene, 1,8-bis(bromomethyl)naphthalene and 1,4-bis(chloromethyl)naphthalene. They may be used alone or in combination of two or more compounds as far as an intramolecular cyclization reaction does not occur.

The equivalent ratio of the halomethyl group of the vinylbenzyl halide to the halomethyl group of the dihalomethyl compound can be selected as far as gelation is not caused by the dihalomethyl compound. The equivalent ratio of the vinylbenzyl halide to the dihalomethyl compound is preferably in the range of 1.0/0 to 0.1/0.9. When the amount of the vinylbenzyl halide is below the above range, curability deteriorates and the physical properties such as heat resistance of the cured product deteriorate.

Examples of the reaction solvent include aprotic polar solvents such as dimethylformamide, dimethyl sulfoxide, dimethyl acetamide, N-methylpyrrolidone, dioxane, acetonitrile, tetrahydrofuran, ethylene glycol dimethyl ether, 1,3-dimethoxypropane, 1,2-dimethoxypropane, tetramethylene sulfone, hexamethyl phosphamide, methyl ethyl ketone, methyl isobutyl ketone, acetone and cyclohexanone, and mixtures thereof. A solvent may be selected from among these according to the types of raw materials and reaction conditions so that a reaction system becomes uniform.

Examples of the alkali used in the present invention include alkoxides, hydrides and hydroxides of an alkali metal or alkali earth metal such as sodium methoxide, sodium ethoxide, sodium hydride, sodium borohydride, potassium hydride and potassium hydroxide. The alkali may be selected according to whether the reaction system is made hydrous or anhydrous.

The amount of the alkali is preferably 1.1 to 3.0 equivalents based on 1 equivalent of the hydrogen atom at the 9-position of the fluorene compound as a raw material. When the amount is less than 1.1 equivalents, the reaction rate becomes very low and the reaction does not proceed completely, with the result that the raw materials remain and an undesirable influence is exerted on the physical properties of the cured product. When the amount is beyond 3 equivalents in use, a large amount of a solvent for removing the residual alkali, such as washing water, must be used, which is not economical.

A phase-transfer catalyst may be used for the reaction in the present invention. Examples of this phase-transfer catalyst include onium salts such as quaternary ammonium compounds including tetra-n-butylammonium bromide, tetra-n-butylammonium hydrogen sulfate, benzyltrimethylammonium chloride and tricaprylmethylammonium chloride, quaternary phosphonium compounds including tetra-n-butylphosphonium bromide, benzyltriphenylphosphonium chloride, tetraphenylphosphonium chloride and tetraphenylphosphonium bromide, and tertiary sulfonium compounds such as benzyltetramethylene sulfonium bromide, and mixtures thereof.

The amount of the phase-transfer catalyst used cannot be completely specified because catalytic effect differs according to the type of catalyst or the reaction temperature. However, it is generally about 0.01 to 0.2 equivalent based on 1 equivalent of the hydrogen atom at the 9-position of the fluorene compound as a raw material.

The reaction temperature and reaction time cannot be completely specified because they differ according to the types of raw material compound and the reaction conditions but may be preferably 30 to 100° C. and 0.5 to 20 hours, respectively. When the reaction temperature is higher than 100° C., an unpreferred reaction such as thermal polymerization occurs and when the reaction temperature is lower than 30° C., though the reaction proceeds, it takes a long time, which is not economical.

Since a highly polymerizable unsaturated halide such as vinylbenzyl halide is used in the present invention, a thermal polymerization inhibitor may be optionally added to the reaction system. Examples thereof include t-butylcatechol, 2,4-di-t-butylphenol, 2-t-butylphenol, 2-t-butyl-4-nitrophenol, 2,4-dinitrophenol, hydroquinone, methyl hydroquinone, hydroquinone monomethyl ether, t-butylhydroquinone, resorcin, pyrogallol, phenothiazine or copper salt. Further, use of a suitable amount of air is effective in inhibiting polymerization.

The amount of the thermal polymerization inhibitor used cannot be completely specified because its effect differs according to the type of thermal polymerization inhibitor. However, an inhibitor of several ppm to 2,000 ppm based on the curable vinylbenzyl compound is sufficient.

The curable polyvinyl benzyl compound represented by the above general formula 1 of the present invention is obtained by the above production process. In the general formula 1, the divalent organic group of $R^1$ is derived from the carbon chain of the dihalomethyl compound. Also, n may be duly determined according to the desired degree of polymerization and mechanical strength and $R^2$ is determined according to the type of fluorene compound.

The curable polyvinyl benzyl compound of the present invention may be mixed with a monomer, oligomer and/or polymer copolymerizable with the above compound without departing from the gist of the present invention to prepare a curable resin composition having improved moldability. Specific examples of the monomer, oligomer and polymer include oligomers and polymers having a polymerizable unsaturated group, such as vinyl ester resins, unsaturated polyester resins, diallyl phthalate resins, maleimide resins and polycyanate resins of polyphenol, monomers and prepolymers such as triallyl isocyanurate and triallyl cyanurate, styrene, vinyltoluene, divinylbenzene, vinylbenzyl ether compounds, and monofunctional and polyfunctional (meth) acrylic acid derivative compounds.

The total use amount of the above copolymerizable monomer, oligomer and/or polymer cannot be completely specified because it differs according to the types thereof, compatibility with the vinylbenzyl compound and the intended application of the cured product. It is 0 to 300 parts by weight, preferably 0 to 200 parts by weight based on 100 parts by weight of the curable polyvinyl benzyl compound. It is more preferably 10 to 100 parts by weight. An addition amount beyond 300 parts by weight is undesirable because separation and exudation from the curable polyvinyl benzyl compound readily occur.

The curable polyvinyl benzyl compound and curable resin composition of the present invention can be cured by a known method such as heat, light or an electron beam. It is also useful to reduce the curing temperature or promote a curing reaction by using a curing agent. The cured product can be suitably used in organic insulating materials, etc. for use in electronic equipment such as communications equipment.

When a curing agent is used, benzoyl peroxide, cumene hydroperoxide, 2,5-dimethyl-2,5-di(t-butylperoxy)hexine-3, t-butylcumyl peroxide, methyl ethyl ketone peroxide, dicumyl peroxide or t-butyl perbenzoate for example, may be used according to the intended application.

The amount of the curing agent used differs according to the type and content of an unsaturated group contained in the curable polyvinyl benzyl compound or the curable resin composition, the type of the used curing agent, the half-life temperature and required stability, but is generally 0 to 10 parts by weight based on 100 parts by weight of the curable polyvinyl benzyl compound or the curable resin composition.

In addition, a known curing accelerator such as manganese naphthenate, lead naphthenate, zinc naphthenate, cobalt naphthenate, zinc octylate, dimethyl aniline or phenyl morpholine may also be used.

The curing temperature cannot be completely specified because it differs according to the type of the polymerizable unsaturated group and the type and amount of the curing agent used but it is 20 to 250° C., preferably 50 to 250° C. A curing temperature less than 20° C. is undesirable because curing may be insufficient.

A known curing retardant such as hydroquinone, benzoquinone or copper salt may be mixed to adjust curing conditions.

In addition, the curable polyvinyl benzyl compound and/or curable resin composition of the present invention may be optionally mixed with a colorant, filler and reinforcing fiber by a kneader, blender or roll to prepare a molding material or composite material. Silica, alumina, zirconia, titanium dioxide, magnesium hydroxide, aluminum hydroxide or calcium carbonate may be added as the filler without departing from the gist of the present invention.

The above curable polyvinyl benzyl compound or curable resin composition is molded in a desired shape to obtain a high-frequency substrate of the present invention. The high-frequency substrate of the present invention is suitable for use at a high frequency range of 100 MHz or higher, in particular, 1 GHz or higher. The dielectric dissipation factor can be maintained at about 0.002 to 0.01 at this high frequency range.

The present invention further provides a prepreg which is obtained by impregnating the above curable resin composition with a fiber material.

A known fiber material such as glass fiber, carbon fiber, aromatic polyamide fiber, silicon carbide fiber or alumina fiber may be used as the fiber material used in the preparation of the prepreg of the present invention. It is preferably glass cloth formed from a glass fiber having low dielectric properties (a low dielectric constant and a low dielectric dissipation factor). A fiber material content of 30 to 70 wt % based on the prepreg is preferable from the viewpoints of strength and moldability.

In the present invention, to impregnate the curable resin composition with the fiber material, either a known solvent method or a solvent-free method may be used. As for the solvent to be used in the solvent method, a solvent having a relatively low boiling point such as a ketone-based solvent exemplified by acetone, methyl ethyl ketone and methyl isobutyl ketone, or an aromatic hydrocarbon-based solvent exemplified by benzene and toluene may be used in order to reduce the amount of the residual solvent contained in the prepreg as much as possible and avoid a reduction in heat resistance, cracking or the formation of voids.

A prepreg can be obtained by drying and heating the fiber material into which the curable resin composition is impregnated by the above method at 80 to 130° C. for 10 to 180 minutes as required.

A high-frequency substrate can be obtained by heating and pressurizing the obtained single prepreg or a laminate of the prepregs. That is, the high-frequency substrate can be obtained by molding a single prepreg having a predetermined thickness or a laminate of prepregs having a predetermined total thickness by applying heat and pressure in accordance with a known method such as thermal pressing. The molding conditions include a temperature of 80 to 250° C., preferably 100 to 200° C., a pressure of 5 to 100 kg/cm², and a time of 0.5 to 10 hours, for example. It is also effective to increase the temperature stepwise as required.

The present invention also provides a metal-lined high-frequency substrate which is obtained by placing a metal foil on the above prepreg alone or the laminate of the prepregs and applying heat and pressure. That is, a metal-lined high-frequency substrate can be obtained by placing a metal foil on both sides of a single prepreg having a predetermined thickness or a laminate of prepregs having a predetermined total thickness and molding it by applying heat and pressure as described above.

The metal foil used in the present invention can be copper, gold, silver or aluminum foil but is preferably a copper foil. An electrolytic foil or rolled foil may be optionally used.

Further, by applying the above curable resin composition or a solution thereof to a metal foil such as the above copper foil using a doctor blade coating or the like, and drying and heating it at 80 to 130° C. for 10 to 180 minutes, it is also possible to obtain a metal foil having a resin wherein both the foil and the resin composition (or a solution thereof) are integrated. This metal foil may then be used as a high-frequency substrate. A multi-layer laminate substrate may be produced by placing this metal foil having a resin on a core material and molding it by applying heat and pressure.

According to the present invention, there is provided a multi-layer laminate substrate obtained by applying the above curable resin composition onto a conductive layer, polymerizing and curing the composition and further forming a conductive layer on the cured product.

This multi-layer laminate substrate can be manufactured by a so-called build-up process in which an 18 μm-thick copper foil is used as a conductive layer, the curable resin composition is applied onto the conductive layer with a thickness of 20 to 200 μm, preferably 50 to 100 μm as an insulating layer, and thermally cured, and further a conductive layer is formed on the cured product.

The prepreg and the metal foil having a resin obtained by using the above curable resin composition have been described above. The curable vinylbenzyl compound of the present invention may be used in place of the curable resin composition.

A second curable vinylbenzyl compound of the present invention is a compound represented by the following general formula 3:

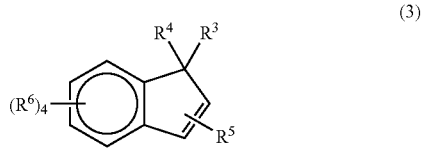

(wherein, $R^3$, $R^4$, and $R^5$ each represent a group selected from the group consisting of a vinylbenzyl group, a hydrogen atom, an alkyl group, alkoxy group, and thioalkoxy group each having 1 to 5 carbon atoms, which may be the same or different, and an aryl group; at least one of $R^3$, $R^4$, and $R^5$ is a vinylbenzyl group; and $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

The second curable vinylbenzyl compound of the present invention can be obtained by reacting at least one indene compound represented by the following general formula 5 and a vinylbenzyl halide in the presence of an alkali:

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

A third curable vinylbenzyl compound of the present invention is a compound represented by the following general formula 4:

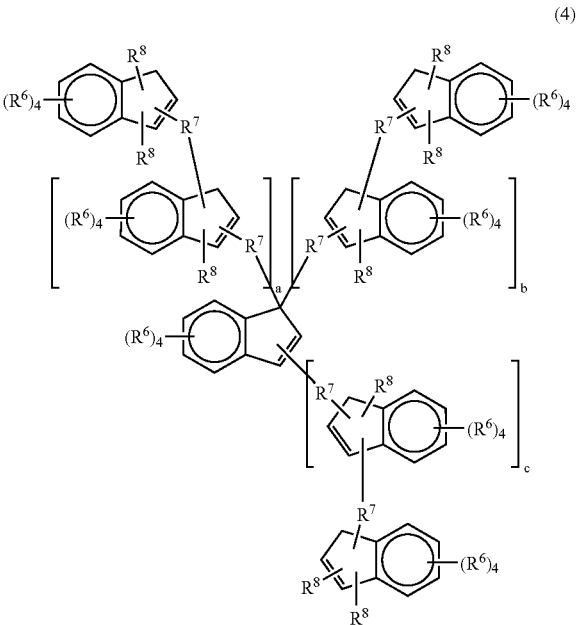

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group; $R^7$ represents a divalent organic group having 2 to 20 carbon atoms; $R^8$ represents a group selected from the group consisting of a vinylbenzyl group, a hydrogen atom, an alkyl group, alkoxy group, and thioalkoxy group each having 1 to 5 carbon atoms, which may be the same or different, and an aryl group; at least one $R^8$ is a vinylbenzyl group; and a, b, and c each represent an integer of 0 to 20).

The third curable vinylbenzyl compound of the present invention can be obtained by reacting at least one indene compound represented by the above general formula 5, a vinylbenzyl halide, and a dihalomethyl compound having 2 to 20 carbon atoms in the presence of an alkali. The dihalomethyl compound used in the present invention is a compound having 2 dihalomethyl groups, that is, 2-$CH_2X$ (where X represents a halogen atom) groups in a molecule.

Further, a fourth curable vinylbenzyl compound of the present invention may be a curable vinylbenzyl compound obtained by reacting at least one indene compound represented by the above general formula 5, a fluorene compound, a vinylbenzyl halide, and a dihalomethyl compound having 2 to 20 carbon atoms in the presence of an alkali.

A vinylbenzylation reaction of the above-mentioned materials in the present invention can be carried out in the presence of an alkali, in an organic solvent or an aqueous solution, preferably in the presence of at least one of an aprotic solvent and a phase-transfer catalyst. The vinylbenzylation reaction is described by L. J. Mathias et al. in J. Polym. Sci., Part B; 36, 2869 (1998) and in J. Polym. Sci., Part A; 35, 587 (1997) and by C. J. Kelly et al. in J. Chem. Res. (S), 446 (1997), for example.

Examples of the indene compound used in the present invention include an indene compound whose indene and aromatic ring parts thereof may be substituted with a halogen atom, an alkyl group, alkoxy group, or thioalkoxy group each having 1 to 5 carbon atoms, or an aryl group as represented by the above general formula 5. The indene compound may be used alone or in combination of two or more compounds. The substituted indene compound may be synthesized easily by halogenating an aromatic part of indene with bromine or the like and introducing a desired group into the halogenated part.

The fluorene compound used in the present invention is preferably a compound represented by the following general formula 6:

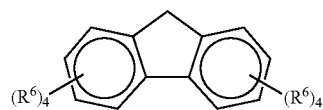

(6)

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

In a case where the fluorene compound is used, an equivalent ratio of the fluorene compound to the indene compound is preferably adjusted to 0.9:0.1 to 0.1:0.9 for a reaction. A large equivalent ratio of the fluorene compound tends to provide a linear compound, and a large equivalent ratio of the indene compound tends to provide a branched compound.

Examples of the vinylbenzyl halide used in the present invention include m-vinylbenzyl chloride, p-vinylbenzyl chloride, m-vinylbenzyl bromide, and p-vinylbenzyl bromide. The vinylbenzyl halide may be used alone or in combination of two or more compounds. Of those, m-vinylbenzyl chloride and p-vinylbenzyl chloride are preferred.

Examples of the organic compound having 2 to 20 carbon atoms containing a dihalomethyl group include: alkylene dihalides such as 1,2-dichloroethane, 1,2-dibromoethane, 1,3-dichloropropane, 1,3-dibromopropane, 1,4-dichlorobutane, and 1,4-dibromobutane; and dihalomethyl compounds such as o-xylylene dichloride, o-xylylene dibromide, m-xylylene dichloride, m-xylylene dibromide, p-xylylene dichloride, p-xylylene dibromide, 4,4'-bis(chloromethyl)biphenyl, 4,4'-bis(chloromethyl)diphenyl ether, 4,4'-bis(chloromethyl)diphenyl sulfide, 2,6-bis(bromomethyl)naphthalene, 1,8-bis(bromomethyl)naphthalene, and 1,4-bis(chloromethyl)naphthalene. The organic compound may be used alone or in combination of two or more compounds as far as an intramolecular cyclization reaction does not occur.

The equivalent ratio of the halomethyl group of the vinylbenzyl halide to the halomethyl group of the dihalomethyl compound having 2 to 20 carbon atoms can be selected as far as gelation is not caused by the dihalomethyl compound. The equivalent ratio of the halomethyl group of the vinylbenzyl halide to the halomethyl group of the dihalomethyl compound having 2 to 20 carbon atoms is preferably adjusted to the range of 0.9:0.1 to 0.1:0.9 for a reaction. An equivalent ratio of the vinylbenzyl halide of less than 0.1 deteriorates curability, thereby deteriorating physical properties of the cured product such as heat resistance.

Examples of the alkali used in the present invention include alkoxides, hydrides, and hydroxides of an alkali metal or an alkali earth metal such as sodium methoxide, sodium ethoxide, sodium hydride, potassium hydride, sodium hydroxide, and potassium hydroxide. The alkali may be selected according to whether a reaction system is a nonaqueous system or a hydrous system.

The amount of the alkali used is preferably 1.1 to 3.0 equivalents with respect to 1 equivalent of the halomethyl group as a raw material. An alkali of less than 1.1 equivalents causes a very low reaction rate and the reaction does not proceed completely, thereby resulting in remained raw materials and providing an adverse effect on the physical properties of the cured product. An alkali used exceeding 3 equivalents requires a large amount of washing water or the like for removing the residual alkali, which is not economical.

Examples of the reaction solvent include: dimethylformamide, dimethyl sulfoxide, dimethyl acetamide, N-methylpyrrolidone, dioxane, acetonitrile, tetrahydrofuran, ethylene glycol dimethyl ether, 1,3-dimethoxypropane, 1,2-dimethoxypropane, tetramethylene sulfone, hexamethylphosphamide, methyl ethyl ketone, methyl isobutyl ketone, acetone, cyclohexanone, methylcyclohexane, toluene, and xylylene; and mixtures thereof. A solvent may be selected from those according to the types of raw materials and reaction conditions for a homogeneous reaction system. Of those, an aprotic polar solvent is preferred.

A phase-transfer catalyst is preferably used in the present invention. Examples of the phase-transfer catalyst include various onium salts. Examples of the onium salts include: quaternary ammonium compounds such as tetra-n-butylammonium bromide, tetra-n-butylammonium hydrogen sulfate, benzyltrimethylammonium chloride, and tricaprylmethylammonium chloride; quaternary phosphonium compounds such as tetra-n-butylphosphonium bromide, benzyltriphenylphosphonium chloride, tetraphenylphosphonium chloride, and tetraphenylphosphonium bromide; tertiary sulfonium compounds such as benzyltetramethylene sulfonium bromide; and mixtures thereof.

The amount of the phase-transfer catalyst used cannot be necessarily specified because catalytic effect differs according to the type of catalyst or the reaction temperature. However, an amount of generally about 0.01 to 0.5 equivalent with respect to 1 equivalent of the halomethyl group of the raw material is sufficient.

The reaction temperature and the reaction time cannot be necessarily specified because they differ according to the type of raw material compound and the reaction conditions but may be preferably 30 to 100° C. and 0.5 to 20 hours, respectively. A reaction temperature exceeding 100° C. may cause an undesirable reaction such as thermal polymerization. Further, a reaction temperature of less than 30° C. requires a long period of time for a reaction, though the reaction proceeds, which is not economical.

The vinylbenzyl halide, which is a highly polymerizable unsaturated halide, is used in the present invention, and thus, a thermal polymerization inhibitor may be optionally added to the reaction system. Examples thereof include t-butylcatechol, 2,4-di-t-butylphenol, 2-t-butylphenol, 2-t-butyl-4-nitrophenol, 2,4-dinitrophenol, hydroquinone, methylhydroquinone, hydroquinone monomethyl ether, t-butylhydroquinone, resorcin, pyrogallol, phenothiazine, and a copper salt. The amount of the thermal polymerization inhibitor used cannot be necessarily specified because its effect differs according to the type of thermal polymerization inhibitor. However, an amount of the thermal polymerization inhibitor of several ppm to 2,000 ppm with respect to the curable vinylbenzyl compound is sufficient.

A curable resin composition of the present invention is prepared by mixing a curable vinylbenzyl compound with a compound copolymerizable with the curable vinylbenzyl compound for improved moldability and for other purposes.

The copolymerizable compound includes a polymer, an oligomer, and a monomer. Specific examples thereof include: polymers such as a vinyl ester resin, an unsaturated polyester resin, a diallyl phthalate resin, a maleimide resin, and a polycyanate resin of polyphenol; oligomers having a polymerizable unsaturated group such as a vinylbenzyl ether resin; monomers and prepolymers such as triallyl isocyanurate and triallyl cyanurate; and vinylbenzyl compounds of fluorene. Further examples thereof include: monomers such as styrene, vinyl toluene, divinylbenzene, and a vinylbenzyl ether compound; and various known monofunctional and polyfunctional (meth)acrylic acid derivative compounds.

The amount of the copolymerizable compound cannot be necessarily specified because it differs according to the type of copolymerizable compound, compatibility with the curable vinylbenzyl compound, the intended application of the cured product, and the like. However, an amount of the copolymerizable compound is 0 to 300 parts by weight, preferably 0 to 200 parts by weight with respect to 100 parts by weight of the curable vinylbenzyl compound. An amount of the copolymerizable compound added exceeding 300 parts by weight is undesirable because separation and exudation from the curable vinylbenzyl compound and the like easily occur.

The curable resin of the present invention is obtained by curing a curable vinylbenzyl compound itself or the curable resin composition.

The curable resin can be cured through a known process such as curing with heat, light, or an electron beam. It is also useful to promote a curing reaction by using a curing agent.

Examples of the curing agent used according to the intended application include benzoyl peroxide, cumene hydroperoxide, 2,5-dimethyl-2,5-di(t-butylperoxy)hexyne-3, t-butylcumyl peroxide, methyl ethyl ketone peroxide, dicumyl peroxide, and t-butyl perbenzoate.

The amount of the curing agent used differs according to the type and concentration of unsaturated group in the curable vinylbenzyl compound or curable resin composition, the type, half-life temperature, and required stability of curing agent used, and the like. However, the amount of the curing agent is generally 0 to 10 parts by weight with respect to 100 parts by weight of the curable vinylbenzyl compound or curable resin composition.

In addition, examples of a known curing accelerator that may be used include manganese naphthenate, lead naphthenate, zinc naphthenate, cobalt naphthenate, zinc octylate, dimethyl aniline, and phenyl morpholine.

The curing temperature cannot be necessarily specified because it differs according to the type of polymerizable unsaturated group and the type, amount, and the like of curing agent used. However, the curing temperature is 20 to 250° C., preferably 50 to 250° C. A curing temperature of less than 20° C. is undesirable because curing may be insufficient.

A known curing retardant such as hydroquinone, benzoquinone, or a copper salt may be mixed to adjust curing conditions.

In addition, at least one of the curable vinylbenzyl compound and curable resin composition of the present invention may be optionally mixed with a colorant, a filler, or a reinforcing fiber using a kneader, a blender, or a roll to prepare a molding material or a composite material. A filler such as silica, alumina, zirconia, titanium dioxide, magnesium hydroxide, aluminum hydroxide, or calcium carbonate may be added within an amount not impairing the effect of the present invention.

The above curable vinylbenzyl compound or curable resin composition of the present invention can be molded into a desired shape to produce a high-frequency substrate. The high-frequency substrate of the present invention is suitable for use at a high frequency range of 100 MHz or higher, particularly 1 GHz or higher. A dielectric dissipation factor can be maintained at about 0.002 to 0.01 in the high frequency range.

Further, a prepreg can be obtained by impregnating a fiber material with the above curable vinylbenzyl compound or curable resin composition.

Examples of a known fiber material which can be used in production of such a prepreg include a glass fiber, a carbon fiber, an aromatic polyamide fiber, a silicon carbide fiber, and an alumina fiber. A glass cloth formed of a glass fiber having low dielectric properties (a low dielectric constant and a low dielectric dissipation factor) is preferably used. A fiber material content is preferably 30 to 70 wt % with respect to the prepreg from the viewpoints of strength, moldability, and the like.

A known solvent process or a solvent-free process may be used to impregnate the fiber material with the curable vinylbenzyl compound or curable resin composition. The solvent used in the solvent process is a solvent having a relatively low boiling point for minimizing the amount of the residual solvent in the prepreg and avoiding reduction in heat resistance and formation of cracking or voids. Examples of the solvent used in the solvent process include: a ketone-based solvent such as acetone, methyl ethyl ketone, or methyl isobutyl ketone; and an aromatic hydrocarbon-based solvent such as benzene or toluene.

A prepreg can be obtained by drying and heating the fiber material impregnated with the curable vinylbenzyl compound or curable resin composition through the above process at 80 to 130° C. for 10 to 180 minutes as required.

A high-frequency substrate can be obtained by heating and pressurizing the obtained single prepreg or a prepreg laminate. That is, a high-frequency substrate can be obtained by: molding a single prepreg having a predetermined thickness or a prepreg laminate having a predetermined total thickness; and molding under heat and pressure through a known process such as thermal pressing. The molding conditions include: a temperature of 80 to 250° C., preferably 100 to 200° C.; a pressure of 5 to 100 kg/cm$^2$; and a time of 0.5 to 10 hours. It is also effective to increase the temperature stepwise as required.

Further, a metal-lined high-frequency substrate can be obtained by: placing a metal foil onto the above prepreg alone or the prepreg laminate; and heating and pressurizing the whole. A metal-lined high-frequency substrate can be obtained by: placing a metal foil on each side of a single prepreg having a predetermined thickness or a prepreg laminate having a predetermined total thickness; and molding the whole under heat and pressure as described above.

Examples of the metal foil used in the present invention include copper, gold, silver, and aluminum foil, but the metal foil is preferably a copper foil. An electrolytic foil or a rolled foil may be optionally used.

Further, a metal foil having a resin in which both a metal foil such as the above copper foil and a resin composition are integrated can be obtained by: applying the above curable vinylbenzyl compound or curable resin composition or a solution thereof to the foil through a doctor blade coating or the like; and drying and heating the whole at 80 to 130° C. for 10 to 180 minutes. The metal foil having a resin may be used as a high-frequency substrate. A multi-layer laminate substrate may be produced by placing the metal foil having a resin on a core material and molding the whole under heat and pressure.

Further, a multi-layer laminate substrate can be produced by: applying the above curable vinylbenzyl compound or curable resin composition onto a conductive layer; polymerizing and curing the composition; and providing an additional conductive layer on the cured product.

Such a multi-layer laminate substrate can be produced through a so-called build-up process involving: using an 18 μm-thick copper foil as a conductive layer; applying the curable vinylbenzyl compound or curable resin composition onto the conductive layer with a thickness of 20 to 200 μm, preferably 50 to 100 μm as an insulating layer; thermally curing the compound or the composition; and forming an additional conductive layer on the cured product.

Hereinafter, the high-frequency substrate of the present invention will be described in detail.

The high-frequency substrate of the present invention is obtained by polymerizing and curing a polymerizable composition, and the polymerizable composition according to the present invention has the following 5 modes:

(1) a composition containing a fluorene compound having at least one polymerizable unsaturated group in a molecule;

(2) a composition containing an indene compound having at least one polymerizable unsaturated group in a molecule;

(3) a composition containing a mixture of a fluorene compound having at least one polymerizable unsaturated group in a molecule and an indene compound having at least one polymerizable unsaturated group in a molecule;

(4) a composition prepared by mixing a fluorene compound having at least one polymerizable unsaturated group in a molecule and a compound copolymerizable with the fluorene compound; and (5) a composition prepared by mixing an indene compound having at least one polymerizable unsaturated group in a molecule and a compound copolymerizable with the indene compound.

First, the mode (1) will be described.

The fluorene compound having at least one polymerizable unsaturated group in a molecule is not particularly limited, but is preferably a compound having at least one of an allyl group and a propargyl group as a polymerizable unsaturated group, or a compound having at least one polymerizable unsaturated group and a vinylbenzyl group.

To be specific, the polymerizable composition of the above mode (1) is preferably a compound obtained by reacting in the presence of an alkali: at least one compound represented by the following general formula 6 as a fluorene compound; a halogen compound having at least one polymerizable unsaturated group selected from the group consisting of a vinylbenzyl halide, an allyl halide, and a propargyl halide; and a dihalomethyl compound having 2 to 20 carbon atoms. Such a compound presumably has the halogen compound and dihalomethyl compound bonded to a ninth position of a fluorene skeleton.

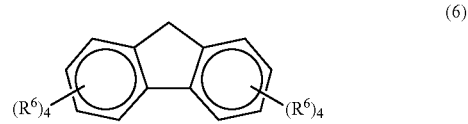

(6)

(wherein, R$^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

Examples of the halogen compound having the polymerizable unsaturated group include m-vinylbenzyl chloride, p-vinylbenzyl chloride, m-vinylbenzyl bromide, p-vinylbenzyl bromide, allyl chloride, allyl bromide, propargyl chloride, and propargyl bromide. The halogen compound may be used alone or in combination of two or more compounds.

The dihalomethyl compound having 2 to 20 carbon atoms is a compound having 2-CH$_2$X (where X is a halogen atom) groups in a molecule. Examples of the dihalomethyl compound include: alkylene dihalides such as 1,2-dichloroethane, 1,2-dibromoethane, 1,3-dichloropropane, 1,3-dibromopropane, 1,4-dichlorobutane, and 1,4-dibromobutane; and dihalomethyl compounds such as o-xylylene dichloride, o-xylylene dibromide, m-xylylene dichloride, m-xylylene dibromide, p-xylylene dichloride, p-xylylene dibromide, 4,4'-bis(chloromethyl)biphenyl, 4,4'-bis(chloromethyl)diphenyl ether, 4,4'-bis(chloromethyl)diphenyl sulfide, 2,6-bis(bromomethyl)naphthalene, 1,8-bis(bromomethyl)naphthalene, and 1,4-bis(chloromethyl)naphthalene. The dihalomethyl compound may be used alone or in combination of two or more compounds as far as an intramolecular cyclization reaction does not occur.

The equivalent ratio of the halomethyl group of the halogen compound having a polymerizable unsaturated group to the halomethyl group of the dihalomethyl compound having 2 to 20 carbon atoms can be selected as far as gelation is not caused by the dihalomethyl compound, but is preferably 0.9/0.1 to 0.1/0.9. An equivalent ratio of the halogen compound having a polymerizable unsaturated group of less than the lower limit deteriorates curability, thereby deteriorating physical properties of the cured product such as heat resistance.

Examples of the reaction solvent include: dimethylformamide, dimethyl sulfoxide, dimethyl acetamide, N-methylpyrrolidone, dioxane, acetonitrile, tetrahydrofuran, ethylene glycol dimethyl ether, 1,3-dimethoxypropane, 1,2-dimethoxypropane, tetramethylene sulfone, hexamethylphosphamide, methyl ethyl ketone, methyl isobutyl ketone, acetone, cyclohexanone, methylcyclohexane, toluene, and xylylene; and mixtures thereof. A solvent may be selected from those according to the types of raw materials and the reaction conditions for a homogeneous reaction system.

Examples of the alkali used in the present invention include alkoxides, hydrides, and hydroxides of an alkali metal or an alkali earth metal such as sodium methoxide, sodium ethoxide, sodium hydride, potassium hydride, sodium hydroxide, and potassium hydroxide. The alkali may be selected according to whether a reaction system is a nonaqueous system or a hydrous system.

The amount of the alkali used is preferably 1.1 to 3.0 equivalents with respect to 1 equivalent of the halomethyl group as a raw material. An alkali of less than 1.1 equivalents causes a very low reaction rate and the reaction does not proceed completely, thereby resulting in remained raw materials and providing an adverse effect on the physical properties of the cured product. An alkali used exceeding 3 equivalents requires a large amount of washing water or the like for removing the residual alkali, which is not economical.

A phase-transfer catalyst may be used for a reaction carried out in the presence of an alkali. Examples of the phase-transfer catalyst include various onium salts. Examples of the onium salts include: quaternary ammonium compounds such as tetra-n-butylammonium bromide, tetra-n-butylammonium hydrogen sulfate, benzyltrimethylammonium chloride, and tricaprylmethylammonium chloride; quaternary phosphonium compounds such as tetra-n-butylphosphonium bromide, benzyltriphenylphosphonium chloride, tetraphenylphosphonium chloride, and tetraphenylphosphonium bromide; tertiary sulfonium compounds such as benzyltetramethylene sulfonium bromide; and mixtures thereof.

The amount of the phase-transfer catalyst used cannot be necessarily specified because a catalytic effect differs according to the type of catalyst or the reaction temperature. However, an amount of generally about 0.01 to 0.5 equivalent with respect to 1 equivalent of the halomethyl group of the raw material is sufficient.

The reaction temperature and the reaction time cannot be necessarily specified because they differ according to the type of raw material compound and the reaction conditions but may be preferably 30 to 100° C. and 0.5 to 20 hours, respectively. A reaction temperature exceeding 100° C. may cause an undesirable reaction such as thermal polymerization. Further, a reaction temperature of less than 30° C. requires a long period of time for a reaction, though the reaction proceeds, which is not economical.

A polymerization inhibitor may be optionally added to the reaction system. Examples thereof include t-butylcatechol, 2,4-di-t-butylphenol, 2-t-butylphenol, 2-t-butyl-4-nitrophenol, 2,4-dinitrophenol, hydroquinone, methylhydroquinone, hydroquinone monomethyl ether, t-butylhydroquinone, resorcin, pyrogallol, phenothiazine, and a copper salt. The amount of the polymerization inhibitor used cannot be necessarily specified because its effect differs according to the type of polymerization inhibitor. However, an amount of the polymerization inhibitor of several ppm to 2,000 ppm with respect to the curable vinylbenzyl compound is sufficient.

Next, the mode (2) will be described.

The indene compound having at least one polymerizable unsaturated group in a molecule is not particularly limited, but is preferably a compound having at least one of a vinylbenzyl group, an allyl group, and a propargyl group as a polymerizable unsaturated group.

To be specific, the polymerizable composition of the above mode (2) is preferably a compound obtained by reacting in the presence of an alkali: at least one compound represented by the following general formula 5 as an indene compound; a halogen compound having at least one polymerizable unsaturated group selected from the group consisting of a vinylbenzyl halide, an allyl halide, and a propargyl halide; and a dihalomethyl compound having 2 to 20 carbon atoms. Such a compound presumably has the halogen compound and dihalomethyl compound bonded to first and third positions of an indene skeleton.

(5)

(wherein, $R^6$ represents at least one group selected from the group consisting of a hydrogen atom, a halogen atom, an alkyl group, alkoxy group, and thioalkoxy group each having 1 to 5 carbon atoms, which may be the same or different, a thioaryloxy group, and an aryl group).

The halogen compound having the polymerizable unsaturated group, the dihalomethyl compound having 2 to 20 carbon atoms, the equivalent ratio of both the compounds, the reaction solvent, the alkali, the phase-transfer catalyst, the reactions conditions, and the like are the same as those in the above mode (1).

Next, the mode (3) will be described.

In the mode (3), the fluorene compound having at least one polymerizable unsaturated group in a molecule and the indene compound having at least one polymerizable unsaturated group in a molecule are the same as those in the above modes (1) and (2). In this case, a mixing ratio of the fluorene compound to the indene compound is 0.1/0.9 to 0.9/0.1 (in weight ratio).

Next, the mode (4) will be described.

In the mode (4), the fluorene compound having at least one polymerizable unsaturated group in a molecule is the same as that in the above mode (1).

The compound copolymerizable with the fluorene compound includes a polymer, an oligomer, and a monomer. Specific examples thereof include: polymers such as a vinyl ester resin, an unsaturated polyester resin, a diallyl phthalate resin, a maleimide resin, and a polycyanate resin of polyphenol; oligomers having a polymerizable unsaturated group such as a vinylbenzyl ether resin; monomers and prepolymers such as triallyl isocyanurate and triallyl cyanurate; and vinylbenzyl compounds of fluorene. Further examples thereof include: monomers such as styrene, vinyl toluene, divinylbenzene, and a vinylbenzyl ether compound; and various known monofunctional and polyfunctional (meth)acrylic acid derivative compounds.

The amount of the copolymerizable compound cannot be necessarily specified because it differs according to the type of copolymerizable compound, compatibility, the intended application of the cured product, and the like. However, an amount of the copolymerizable compound is 0 to 300 parts by weight, preferably 0 to 100 parts by weight with respect to 100 parts by weight of the fluorene compound. An amount of the copolymerizable compound used exceeding 300 parts by weight is undesirable because deterioration of dielectric properties, separation and exudation from the compound, and the like easily occur.

Next, the mode (5) will be described.

In the mode (5), the indene compound having at least one polymerizable unsaturated group in a molecule is the same as that in the above mode (2). The compound copolymerizable with the indene compound and the amount thereof used are the same as those in the above mode (4).

The dielectric constants or flame retardance of the polymerizable compositions of the 5 modes may be controlled by mixing a filler or a flame retardant using a kneader, a blender, a roll, or the like. Examples of the filler include silica, alumina, zirconia, titanium dioxide, magnesium hydroxide, aluminum hydroxide, calcium carbonate, and various dielectric ceramics. Examples of the flame retardant include commercially available halogen-based, phosphorus-based, and nitrogen-based flame retardants.

The polymerizable composition can be polymerized and cured through a known process such as polymerizing and curing with heat, light, or an electron beam. It is also useful to promote a curing reaction by using a curing agent.

The curing temperature cannot be necessarily specified because it differs according to the type of polymerizable unsaturated group and the type, amount, and the like of curing agent used. However, the curing temperature is 20 to 250° C., preferably 50 to 250° C. A curing temperature of less than 20° C. is undesirable because curing may be insufficient.

Examples of the curing agent used according to the intended application include benzoyl peroxide, cumene hydroperoxide, 2,5-dimethyl-2,5-di(t-butylperoxy)hexyne-3, t-butylcumyl peroxide, methyl ethyl ketone peroxide, dicumyl peroxide, and t-butyl perbenzoate.

The amount of the curing agent used differs according to the type and concentration of unsaturated group in the polymerizable composition, the type, half-life temperature, and required stability of curing agent used, and the like. However, the amount of the curing agent is generally 0 to 10 parts by weight with respect to the composition.

In addition, examples of a known curing accelerator that may be used include manganese naphthenate, lead naphthenate, zinc naphthenate, cobalt naphthenate, zinc octylate, dimethyl aniline, and phenyl morpholine.

A known curing retardant such as hydroquinone, benzoquinone, or a copper salt may be mixed to adjust curing conditions.

The high-frequency substrate of the present invention obtained by polymerizing and curing the polymerizable composition for molding into a desired shape is suitable for use at a high frequency range of 100 MHz or higher, particularly 1 GHz or higher. A dielectric dissipation factor can be maintained at about 0.002 to 0.01 in the high frequency range.

Further, the prepreg of the present invention can be obtained by impregnating a fiber material with the above polymerizable composition.

Examples of a known fiber material which can be used in production of the prepreg of the present invention include a glass fiber, a carbon fiber, an aromatic polyamide fiber, a silicon carbide fiber, and an alumina fiber. A glass cloth formed of a glass fiber having low dielectric properties (a low dielectric constant and a low dielectric dissipation factor) is preferably used. A fiber material content is preferably 30 to 70 wt % with respect to the prepreg from the viewpoints of strength, moldability, and the like.

A known solvent process or a solvent-free process may be used to impregnate the fiber material with the polymerizable composition. The solvent used in the solvent process is a solvent having a relatively low boiling point for minimizing the amount of the residual solvent in the prepreg and avoiding reduction in heat resistance and formation of cracking or voids. Examples of the solvent used in the solvent process include: a ketone-based solvent such as acetone, methyl ethyl ketone, or methyl isobutyl ketone; and an aromatic hydrocarbon-based solvent such as benzene or toluene.

A prepreg can be obtained by drying and heating the fiber material impregnated with the polymerizable composition through the above process at 80 to 130° C. for 10 to 180 minutes as required.

A high-frequency substrate can be obtained by heating and pressurizing the obtained single prepreg or a prepreg laminate. That is, a high-frequency substrate can be obtained by: molding a single prepreg having a predetermined thickness or a prepreg laminate having a predetermined total thickness; and molding under heat and pressure through a known process such as thermal pressing. The molding conditions include: a temperature of 80 to 250° C., preferably 100 to 200° C.; a pressure of 5 to 100 kg/cm$^2$; and a time of 0.5 to 10 hours. It is also effective to increase the temperature stepwise as required.

Further, a metal-lined high-frequency substrate of the present invention is obtained by: placing a metal foil onto the above prepreg alone or the prepreg laminate; and heating and pressurizing the whole. A metal-lined high-frequency substrate can be obtained by: placing a metal foil on each side of a single prepreg having a predetermined thickness or a prepreg laminate having a predetermined total thickness; and molding the whole under heat and pressure as described above.

Examples of the metal foil used in the present invention include copper, gold, silver, and aluminum foil, but the metal foil is preferably a copper foil. An electrolytic foil or a rolled foil may be optionally used.

Further, a metal foil having a resin in which both a metal foil such as the above copper foil and the polymerizable composition are integrated can be obtained by: applying the polymerizable composition or a solution thereof to the foil through a doctor blade coating or the like; and drying and heating the whole at 80 to 130° C. for 10 to 180 minutes. The metal foil having a resin may be used as a high-frequency substrate. A multi-layer laminate substrate may be produced by placing the metal foil having a resin on a core material and molding the whole under heat and pressure.

Further, a multi-layer laminate substrate is obtained by: applying the above polymerizable composition onto a conductive layer; polymerizing and curing the composition; and providing an additional conductive layer on the cured product.

Such a multi-layer laminate substrate can be produced through a so-called build-up process involving: using an 18 μm-thick copper foil as a conductive layer; applying the polymerizable composition onto the conductive layer with a thickness of 20 to 200 μm, preferably 50 to 100 μm as an insulating layer; thermally curing the compound or the composition; and forming an additional conductive layer on the cured product.

BEST MODE FOR CARRYING OUT THE INVENTION

Hereinafter, the present invention will be described based on examples and comparative examples. However, the present invention is not limited to those examples. The term "parts" in the examples means "parts by weight" unless otherwise stated. Measurement methods carried out in Examples 1 to 4 and Comparative Examples 1 and 2 are shown below.

(1) Weight reduction start temperature: measured under a nitrogen flow at a temperature increase rate of 10° C./min using TG/DTA6200 available from SII Co., Ltd.

(2) Dielectric properties: measured using the 4285A and 4285B LCR meters available from Yokogawa Hewlett Packard Co., Ltd. in accordance with an equilibrium bridge method (1 MHz).

(3) $^1$H-nuclear magnetic resonance spectrum ($^1$H-NMR): measured using tetramethylsilane as an internal standard material and the JNM-LA300 available from JEOL Ltd.

(4) IR spectrum: measured using the Fourier Transform Infrared Spectrophotometer, JIR-RFX3002 FT-IR SPECTROPHOTOMETER available from JEOL Ltd.

(5) Gel permeation chromatography (GPC): The molecular weight (Mw) in terms of standard polystyrene was measured at a column temperature of 40° C. and an elution rate of 1 ml/min using tetrahydrofuran as an eluate and the Shodex GPC System-21 (column KF-802, KF-803, KF-805) available from Showa Denko K.K.

(6) Water absorption: calculated from dry weight and weight after the absorption of water by immersing a test specimen measuring 1.5 mm×50 mm×50 mm in water at 25° C. for 24 hours.

EXAMPLE 1

49.8 g (0.3 mol) of fluorene, 200 g of methylisobutyl ketone, 2.91 g (9×10$^{-3}$ mol) of tetra-n-butylammonium bromide, 0.73 g of hydroquinone and 96 g of a 50 wt % aqueous solution of NaOH (NaOH purity of 95%, 1.14 mol) were charged into a 1-liter four-necked flask equipped with a thermoregulator, stirrer, cooling condenser and dropping funnel and heated at 62° C. under agitation to prepare a uniform solution. 117 g of vinylbenzyl chloride CMS-AM (m-/p-isomers: 50/50 wt % mixture) available from Seimi Chemical Co., Ltd. (purity of 91%, 0.7 mol) was added dropwise to this dark blue green solution over 20 minutes and then a reaction was carried out at 60 to 61° C. for 7 hours. After 200 ml of toluene was added to the obtained green reaction product, the obtained solution was neutralized with 2N hydrochloric acid and washed with distilled water three times, toluene was removed under reduced pressure, and the obtained light yellow viscous solid was recrystallized from fresh toluene to obtain 73.4 g of a gray white solid having a melting point measured by DSC of 142° C. (yield of 61.5%). This is designated as compound 1.

Figure 1:
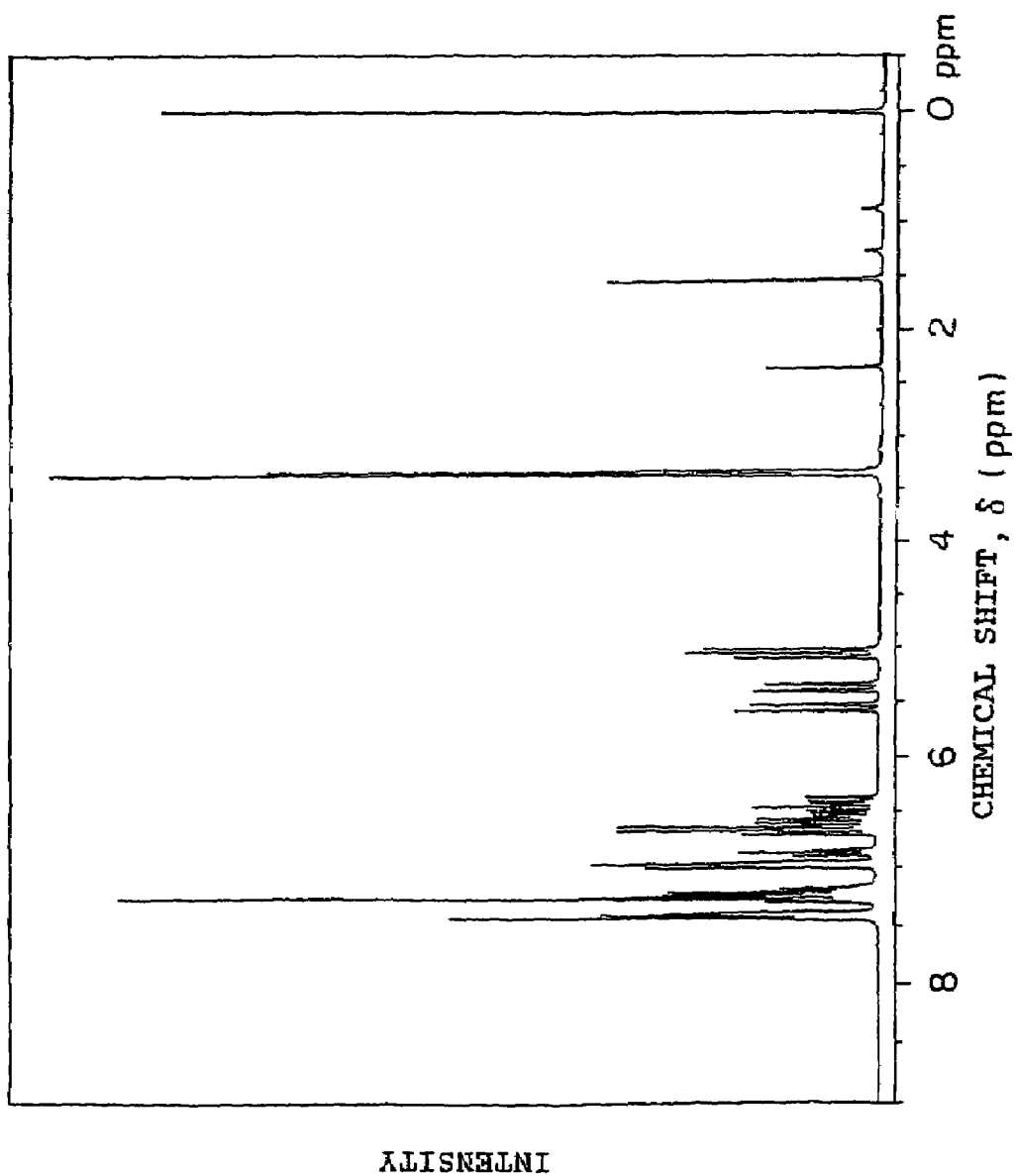
FIG. 1 shows an $^1$H-NMR spectrum of a compound 1 obtained in Example 1.
Figure 2:
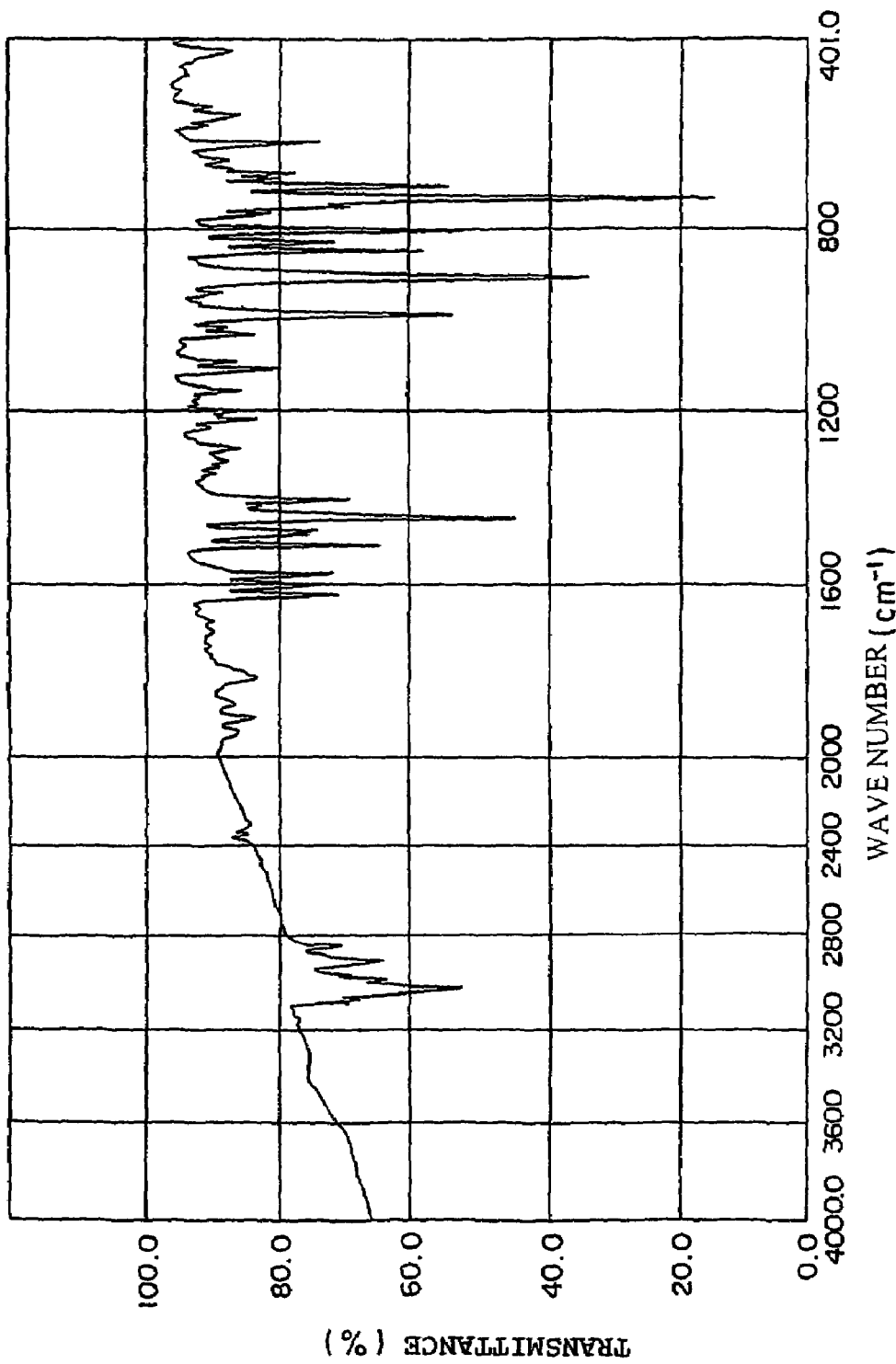
FIG. 2 shows an IR spectrum of the compound 1 obtained in Example 1.

Compound 1 was identified from its $^1$H-NMR spectrum, IR spectrum and GPC measurement. FIG. 1 shows the $^1$H-NMR spectrum and FIG. 2 shows the IR spectrum. It was found from the GPC measurement results that the product had an Mw of 400 and it was judged from these measurement results that the product was 9,9-bis(vinylbenzyl)fluorene (in the general formula 1, $R^2$ is a hydrogen atom and n=0).

The compound 1 was placed in a mold heated at 150° C. and press-cured at 150° C. with a pressure of 4.9 MPa to 7.8 MPa (50 to 80 kgf/cm$^2$) for 1 hour and at 180° C. with the same pressure for 5 hours to manufacture a resin plate so as to prepare test specimens required for each measurement. The measurement results are shown in Table 1.

EXAMPLE 2

Figure 3:
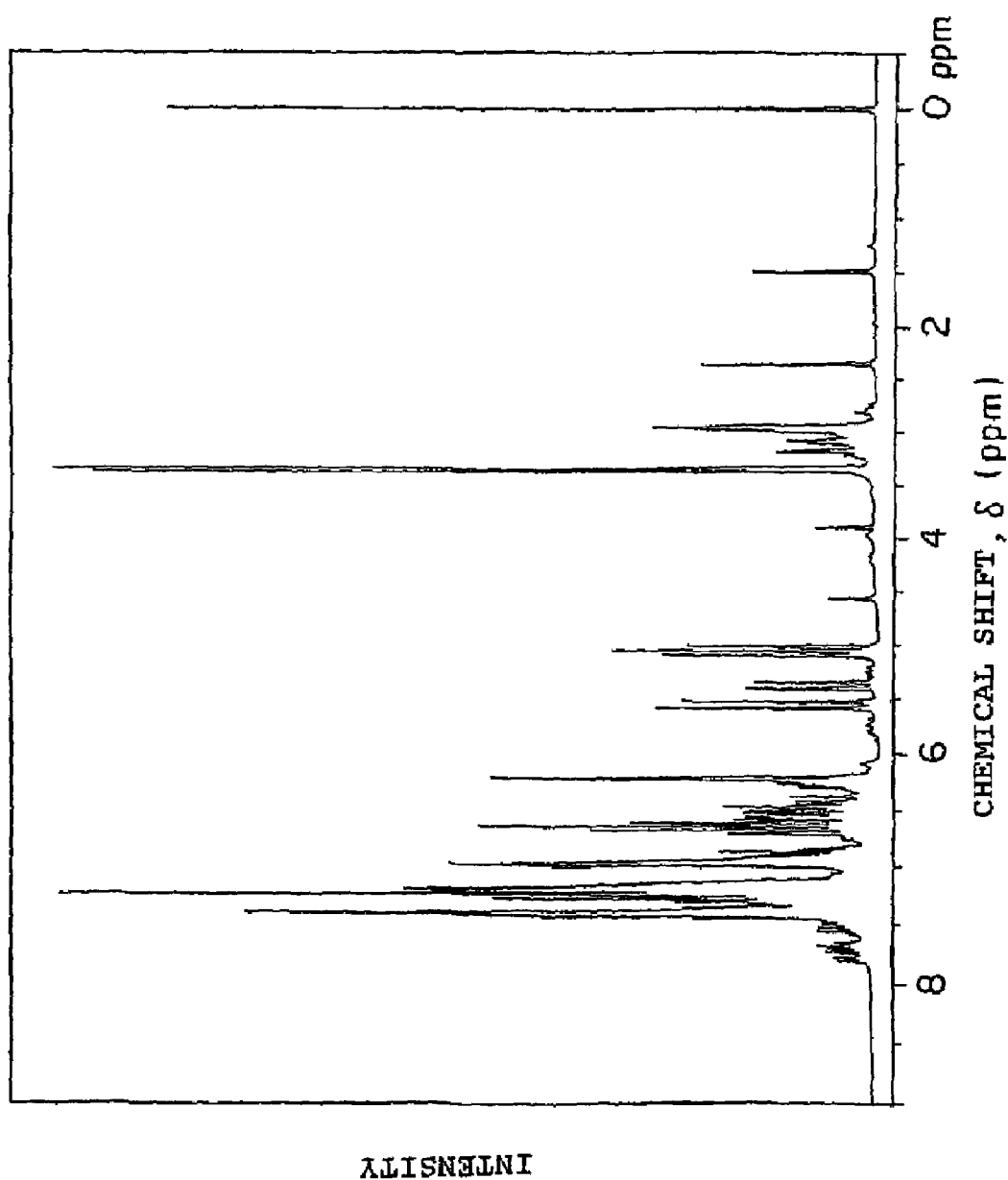
FIG. 3 shows the $^1$H-NMR spectrum of a compound 2 obtained in Example 2.
Figure 4:
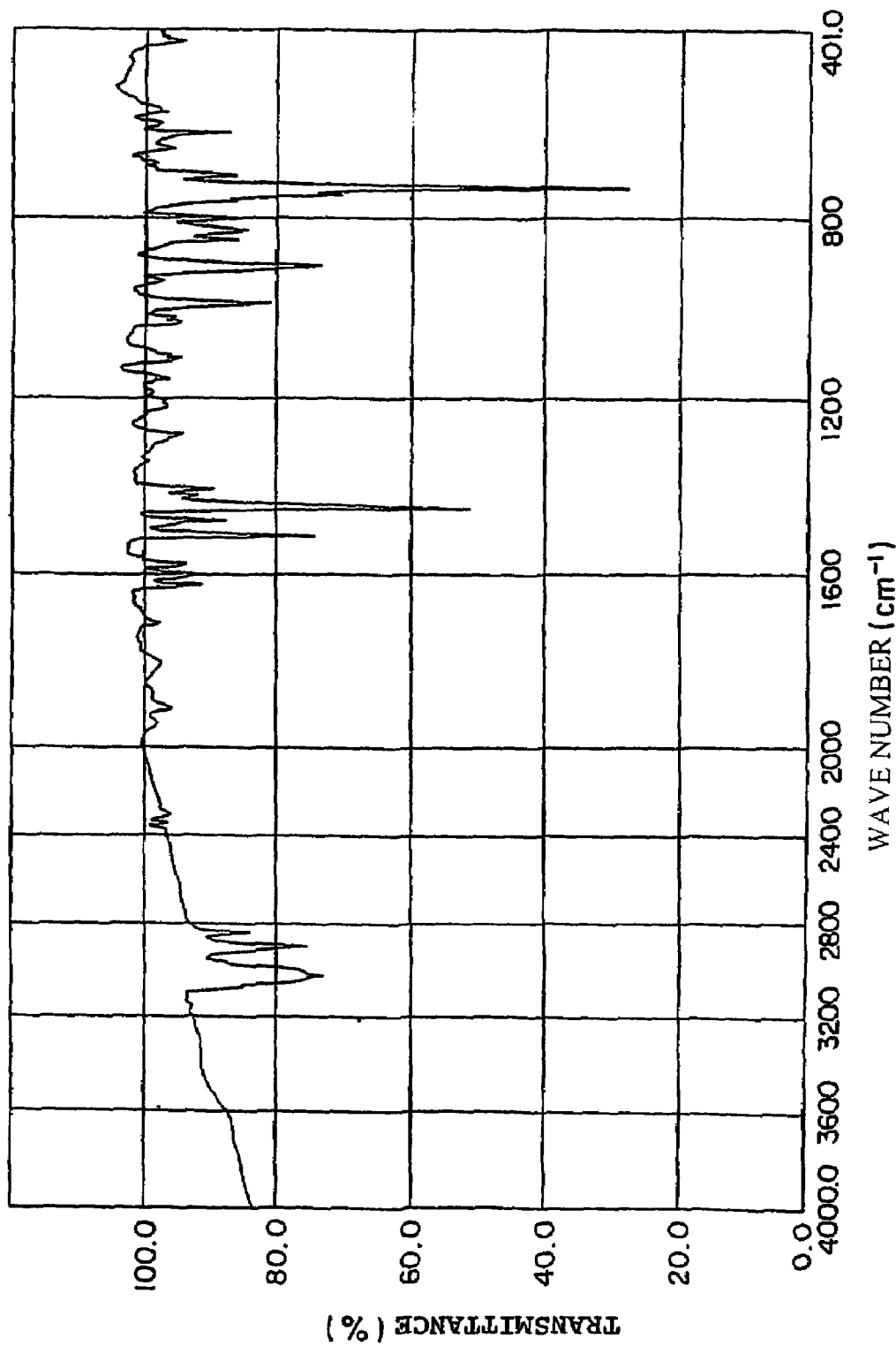
FIG. 4 shows the IR spectrum of the compound 2 obtained in Example 2.

49.8 g (0.3 mol) of fluorene, 220 g of toluene, 2.91 g (9×10$^{-3}$ mol) of tetra-n-butylammonium bromide and 96 g of a 50 wt % aqueous solution of NaOH (purity of 95%, 1.14 mol) were added to the reactor used in Example 1 and heated at 65° C., and 21 g (0.12 mol) of p-xylylene dichloride was added, and reacted for 2.5 hours. After it was confirmed from the results of the $^1$H-NMR measurement of a small amount of the reaction product that p-xylylene dichloride was consumed, 54 g of CMS-AM (purity of 91%, 0.36 mol) was added dropwise to the reaction system and the reaction was continued at 65° C. for 6.5 hours. After the reaction solution was cooled to room temperature, 2N hydrochloric acid was added to neutralize the reaction mixture, and distilled water was added to the organic layer, which was then washed three times. After the solvent was distilled off under reduced pressure, the obtained solid was pulverized and filtered in methanol to collect solid matter through filtration, which was then dried at 50° C. in a vacuum oven to obtain a curable polyvinyl benzyl compound at a yield of 90%. The molecular weight Mw measured by GPC of the compound was 3,100. The melting point measured by DSC of the compound was 75 to 120° C. This is designated as compound 2. FIG. 3 shows the $^1$H-NMR spectrum of this compound and FIG. 4 shows the IR spectrum of the compound. Compound 2 is a compound of the general formula 1 in which $R^1$ is a xylylene group, $R^2$ is a hydrogen atom and n=about 10 (mixed with a compound in which n=0).

Compound 2 was then poured into the gap between glass plates and cured at 130° C. for 2 hours, at 160° C. for 2 hours and after-cured at 180° C. for 5 hours. Test specimens required for each measurement were prepared from the obtained resin plate. The measurement results are shown in Table 1.

EXAMPLE 3

A solution containing 60 wt % of Compound 2 synthesized in Example 2 and 40 wt % of divinyl benzene (purity of 82%) was prepared, poured into the gap between glass plates and cured at 100° C. for 6 hours, at 160° C. for 4 hours and after-cured at 180° C. for 2 hours. Test specimens required for each measurement were prepared from the obtained resin plate. The results are shown in Table 1.

COMPARATIVE EXAMPLE 1

45 g (0.25 equivalent) of dicyclopentadiene skeleton phenolic resin, DPP-3H (special phenolic resin manufactured by Nippon Petrochemical Co., Ltd.), 38.1 g of vinylbenzyl chloride CMS-AM (m-/p-isomers: 50/50 wt % mixture) (purity of 91%, 0.25 mol), 2.4 g of tetra-n-butylammonium bromide, 0.038 g of 2,4-dinitrophenol and 200 g of methyl ethyl ketone were charged into a 1-liter four-necked flask equipped with a thermoregulator, stirrer, cooling condenser and dropping funnel and dissolved under agitation, and 40 g of a 50 wt % aqueous solution of NaOH (NaOH purity of 95%, 0.475 mol) was added dropwise at 75° C. to the obtained solution over 20 minutes and further stirred at 75° C. for 4 hours. After the obtained reaction mixture was cooled to room temperature, it was neutralized with 2N hydrochloric acid, 100 g of toluene was added, and the organic layer was then washed three times with 300 g of distilled water. After methyl ethyl ketone was removed under reduced pressure, the reaction product was precipitated in 300 ml of methanol to collect solid matter through filtration, which was then dried at 50° C. in a vacuum oven to obtain a vinylbenzyl ether compound at a yield of 95%. This is designated as compound 3.

Compound 3 was cured and molded in the same manner as in Example 1 to prepare a resin plate. Test specimens required for each measurement were prepared from this resin plate. The measurement results are shown in Table 1.

COMPARATIVE EXAMPLE 2

2 parts of 2-ethyl-4-methylimidazole (available from Shikoku Kasei Co., Ltd.) was mixed with 100 parts of an epoxy resin (Epicoat 828, available from Yuka Shell Epoxy Co., Ltd. (epoxy equivalent 188), to prepare a resin composition. This is designated as compound 4.

Compound 4 was poured into the gap between glass plates and cured at 80° C. for 2 hours and after-cured at 150° C. for 2 hours to manufacture a resin plate. Test specimens required for each measurement were prepared from this resin plate. The measurement results are shown in Table 1.

EXAMPLE 4

54.1 g (0.3 mol) of 1-methylfluorene, 200 g of methylisobutyl ketone, 2.91 g ($9 \times 10^{-3}$ mol) of tetra-n-butylammonium bromide, 0.73 g of hydroquinone and 96 g of a 50 wt % aqueous solution of NaOH (NaOH purity of 95%, 1.14 mol) were charged into a 1-liter four-necked flask equipped with a thermoregulator, stirrer, cooling condenser and dropping funnel and heated at 62° C. under agitation to prepare a uniform solution. 117 g of vinylbenzyl chloride, CMS-AM (m-/p-isomers: 50/50 wt % mixture) available from Seimi Chemical Co., Ltd. (purity of 91%, 0.7 mol) was added dropwise to this dark blue green solution over 20 minutes, which was then reacted at 60 to 61° C. for 7 hours. After 200 ml of toluene was added to the obtained green reaction product, the obtained solution was neutralized with 2N hydrochloric acid and washed three times with distilled water, toluene was removed under reduced pressure, and the obtained light yellow viscous solid was recrystallized from fresh toluene to obtain 75.1 g of a gray white solid having a melting point measured by DSC of 142° C. (yield of 60.8%). This is designated as compound 5.

Figure 5:
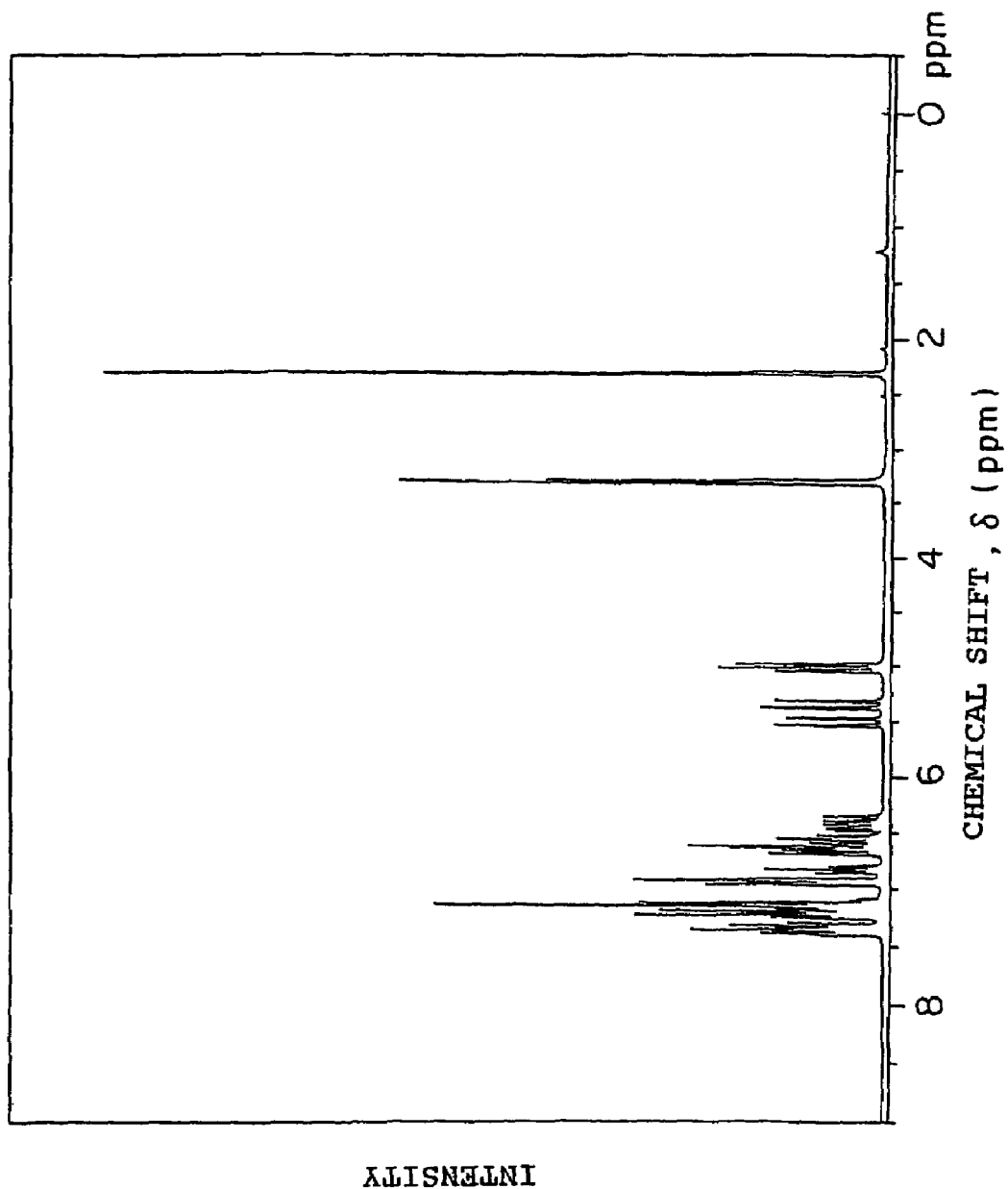
FIG. 5 shows the $^1$H-NMR spectrum of a compound 5 obtained in Example 4.

Compound 5 was identified from its $^1$H-NMR spectrum, IR spectrum and GPC measurement. FIG. 5 shows the $^1$H-NMR spectrum. It was found from the GPC measurement results that the product had an Mw of 410 and it was judged from these measurement results that the product was 1-methyl-9,9-bis(vinylbenzyl)fluorene.

Compound 5 was placed in a mold heated at 150° C. and press-cured at 150° C. with a pressure of 50 to 80 kgf/cm$^2$ for 1 hour and at 180° C. with the same pressure for 5 hours to manufacture a resin plate so as to prepare test specimens required for each measurement. The measurement results are shown in Table 1.

TABLE 1

| Mixing ratio | Example 1 | Example 2 | Example 3 | Comparative Example 1 | Comparative Example 2 | Example 4 |
| --- | --- | --- | --- | --- | --- | --- |
| Compound 1 | 100 parts | | | | | |
| Compound 2 | | 100 parts | 60 parts | | | |
| Compound 3 | | | | 100 parts | | |
| Compound 4 | | | | | 100 parts | |
| Compound 5 | | | | | | 100 parts |
| Divinylbenzene | | | 40 parts | | | |
| Cured product physical properties | | | | | | |
| 5% weight reduction temperature | 392° C. | 364° C. | 378° C. | 371° C. | 399° C. | 386° C. |
| Water absorption | 0.12% | 0.11% | 0.12% | 0.16% | 1.4% | 0.14% |
| Dielectric constant (1 MHz) | 2.65 | 2.67 | 2.79 | 2.82 | 3.29 | 2.69 |
| Dielectric dissipation factor (1 MHz) | 0.0013 | 0.0023 | 0.0017 | 0.0070 | 0.0249 | 0.0015 |

It is understood from the results of Table 1 that the curable polyvinyl benzyl compound of the present invention attains better dielectric properties (lower dielectric constant and lower dielectric dissipation factor) than the conventional resins of the comparative examples without impairing heat resistance and has stable dielectric properties because of its lower water absorption.

EXAMPLE 5

The glass cloth, WEA18K105BZ2 (available from Nitto Boseki Co., Ltd.) was impregnated with a 60% toluene solution of Compound 1 and dried at 120° C. for 60 minutes to obtain a prepreg. A 10-ply laminate of the prepregs was prepared and molded through the application of heat and pressure (40 kg/cm$^2$) at 150° C. for 2 hours, at 180° C. for 5 hours and at 200° C. for 5 hours to obtain a laminated plate having a thickness of 1.6 mm and a glass fiber content of 60%.

The dielectric properties and solder heat resistance of this laminated plate were tested by the methods desirable below. As a result, the plate had a dielectric constant of 4.0, a dielectric dissipation factor of 0.0035 and a solder heat resistance of 120 seconds or more.

Dielectric properties: The dielectric constant and dielectric dissipation factor at 5 GHz of a prismatic specimen measuring 1.6 mm×1.5 mm×75 mm were measured by the vector network analyzer, HP8753E available from Hewlett Packard Co., Ltd. in accordance with a cavity resonator perturbation method.

Solder heat resistance test: In accordance with JIS C 0054, the specimen was immersed in a solder bath at 260° C. for 120 seconds to check if there was any change in its surface state or shape.

EXAMPLE 6

The procedure of Example 5 was repeated except that the compound 2 was used in place of compound 1. As a result, the compound had a dielectric constant of 4.0, a dielectric dissipation factor of 0.0040 and a solder heat resistance of 120 seconds or more.

EXAMPLE 7

The procedure of Example 5 was repeated except that the compound 5 was used in place of compound 1. As a result, the compound had a dielectric constant of 4.0, a dielectric dissipation factor of 0.0038 and a solder heat resistance of 120 seconds or more.

EXAMPLE 8

A resin solution prepared by dissolving 100 parts of compound 1 and 120 parts of compound 2 in 80 parts of toluene was applied to a 35 μm-thick copper foil 3EC available from Mitsui Mining & Smelting Co., Ltd. to a thickness of 100 μm, dried at 100° C. for 60 minutes and heated at 120° C. for 2 hours to obtain a semi-cured product (two products were manufactured). These two copper foils having a resin were overlapped in such a manner that their resins were brought into contact with each other and molded through the application of heat and pressure at 150° C. for 2 hours and at 180° C. for 6 hours (40 kg/cm$^2$) to obtain a specimen. In accordance with JIS C 6481, this specimen was then used to measure the copper foil's peel strength, which was 1.2 kgf/cm.

Further, measurement methods carried out in Examples 9 to 15 and Reference Examples 1 and 2 are shown below.

Thermogravimetric analysis: measured in a stream of nitrogen at a temperature increase rate of 10° C./minutes using a TGA instrument available from Seiko Instruments Inc.

Dielectric properties: A dielectric constant and a dielectric dissipation factor at 5 GHz of a prism sample of 1.5 mm×1.5 mm×75 mm were measured using a vector network analyzer HP8753E available from Hewlett-Packard Japan, Ltd. in accordance with a cavity resonator perturbation method.

$^1$H-nuclear magnetic resonance spectrum ($^1$H-NMR): measured using tetramethylsilane as an internal standard material and JNM-LA300 available from JEOL Ltd.

Infrared absorption spectrum (1R): measured using a Fourier transform infrared spectrophotometer JIR-RFX3002 FT-IR available from JEOL Ltd.

High performance liquid chromatography (HPLC): measured using Shodex R$^1$-51 (columns KF-801, KF-802) available from SHOWA DENKO K.K. at an elution rate of 1 ml/minute using tetrahydrofuran as an elute.

Water absorption: obtained by immersing a sample of 1.5 mm×40 mm×40 mm in water at 25° C. for 24 hours and calculating with a calculation formula [(W2−W1)/W1]×100 from the dry weight (W1) of the sample and the weight of the sample after the absorption of water (W2).

EXAMPLE 9

Figure 6:
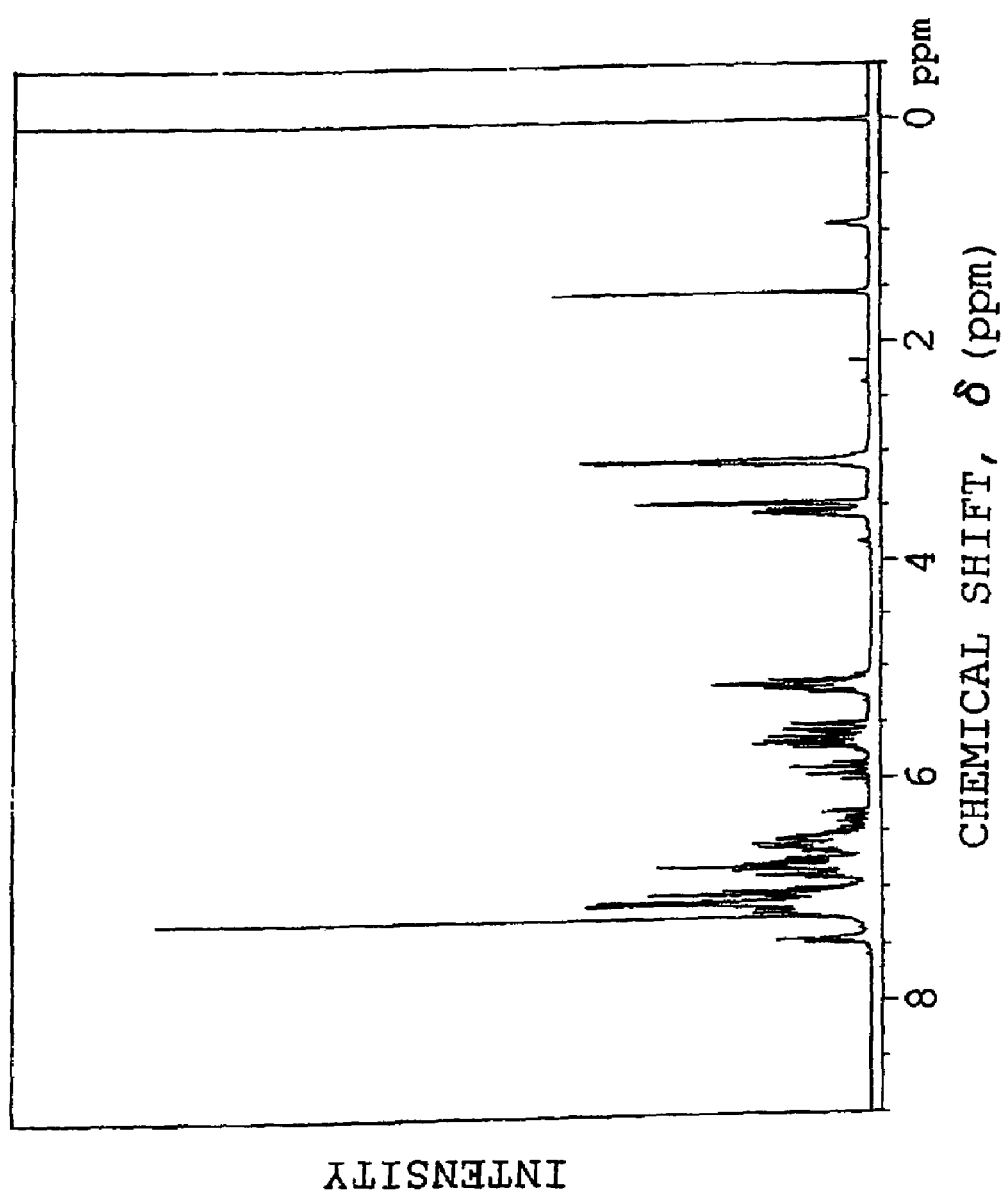
FIG. 6 shows the $^1$H-NMR spectrum of a compound 6 obtained in Example 9.
Figure 7:
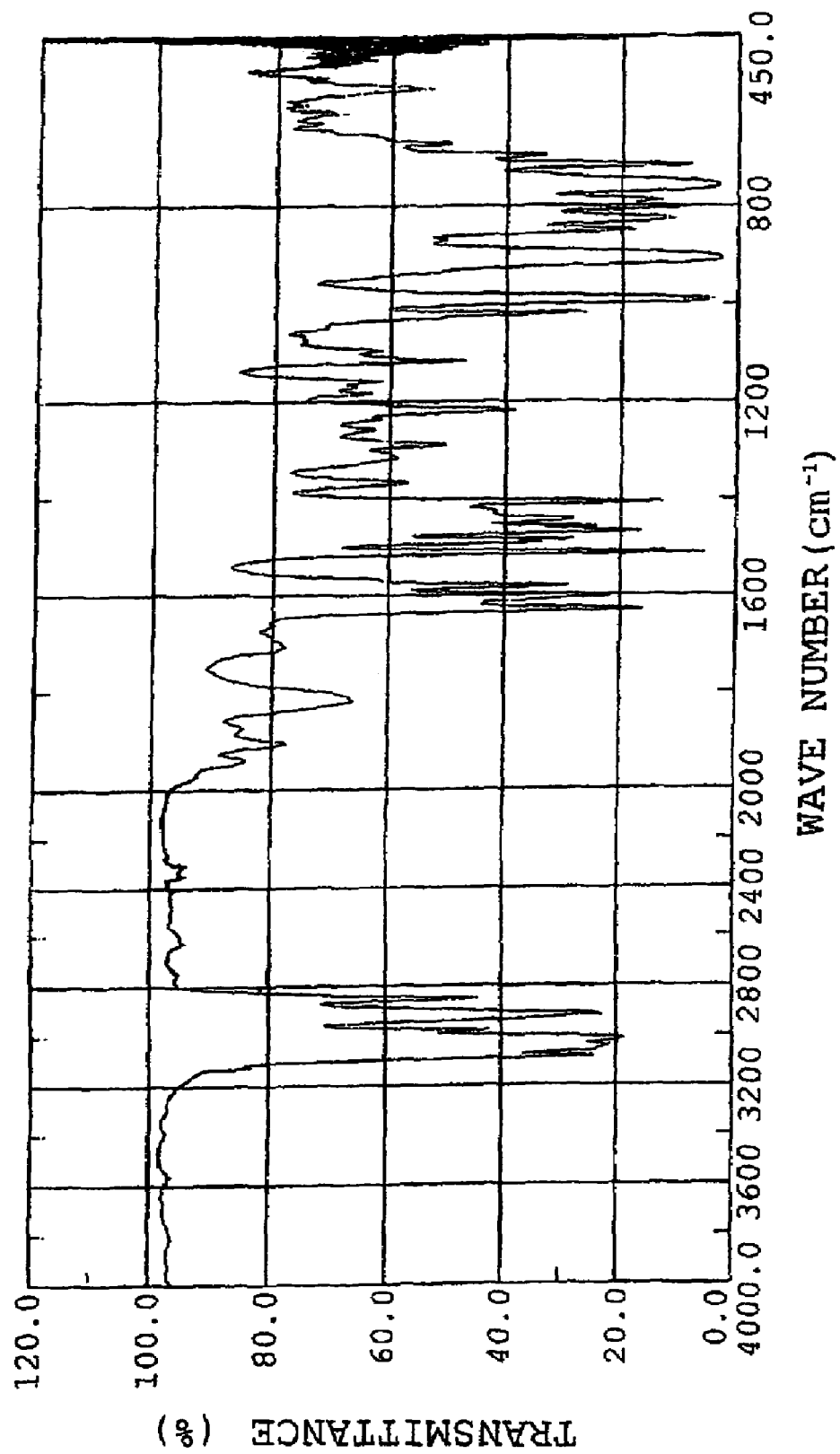
FIG. 7 shows the IR spectrum of a compound 6 obtained in Example 9.

Inside of a flask equipped with a thermoregulator, a stirrer, a cooling condenser, a dropping funnel, and a nitrogen inlet was replaced with nitrogen. 34.9 g (0.3 mol) of indene, 200 g of toluene, 8.72 g (0.027 mol) of tetra-n-butylammonium bromide, 1.79 g (0.009 mol) of phenothiazine, and 144.0 g of a 50 wt % aqueous solution of NaOH (NaOH, 1.8 mol) were charged into the flask and the mixture was heated to 50° C. under stirring, to thereby prepare a homogeneous solution. 150.8 g of vinylbenzyl chloride (CMS-AM; purity of 91%; 0.9 mol; m-/p-isomers: 50/50 wt % mixture; available from Seimi Chemical Co., Ltd.) was added dropwise to the dark blue green solution over 15 minutes, and a reaction was then carried out at 50 to 52° C. for 10 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a curable vinylbenzyl compound of the present invention (mainly composed of a compound in which R$^3$, R$^4$, and R$^5$ each represent a vinylbenzyl group, and R$^6$ represents a hydrogen atom in the general formula 3). The obtained compound is designated as Compound 6. Compound 6 was identified from its $^1$H-NMR spectrum, IR spectrum, and HPLC measurement. Compound 6 was a highly viscous liquid with substantially no fluidity at 23° C. FIG. 6 shows the $^1$H-NMR spectrum, and FIG. 7 shows the IR spectrum.

Compound 6 was poured between glass plates and was cured at 160° C. for 2 hours, at 180° C. for 2 hours, and then at 200° C. for 3 hours to form a resin plate having a thickness of 1.5 mm. Samples required for each measurement were prepared using the resin plate. Table 2 shows the results of the measurements.

EXAMPLE 10

Figure 8:
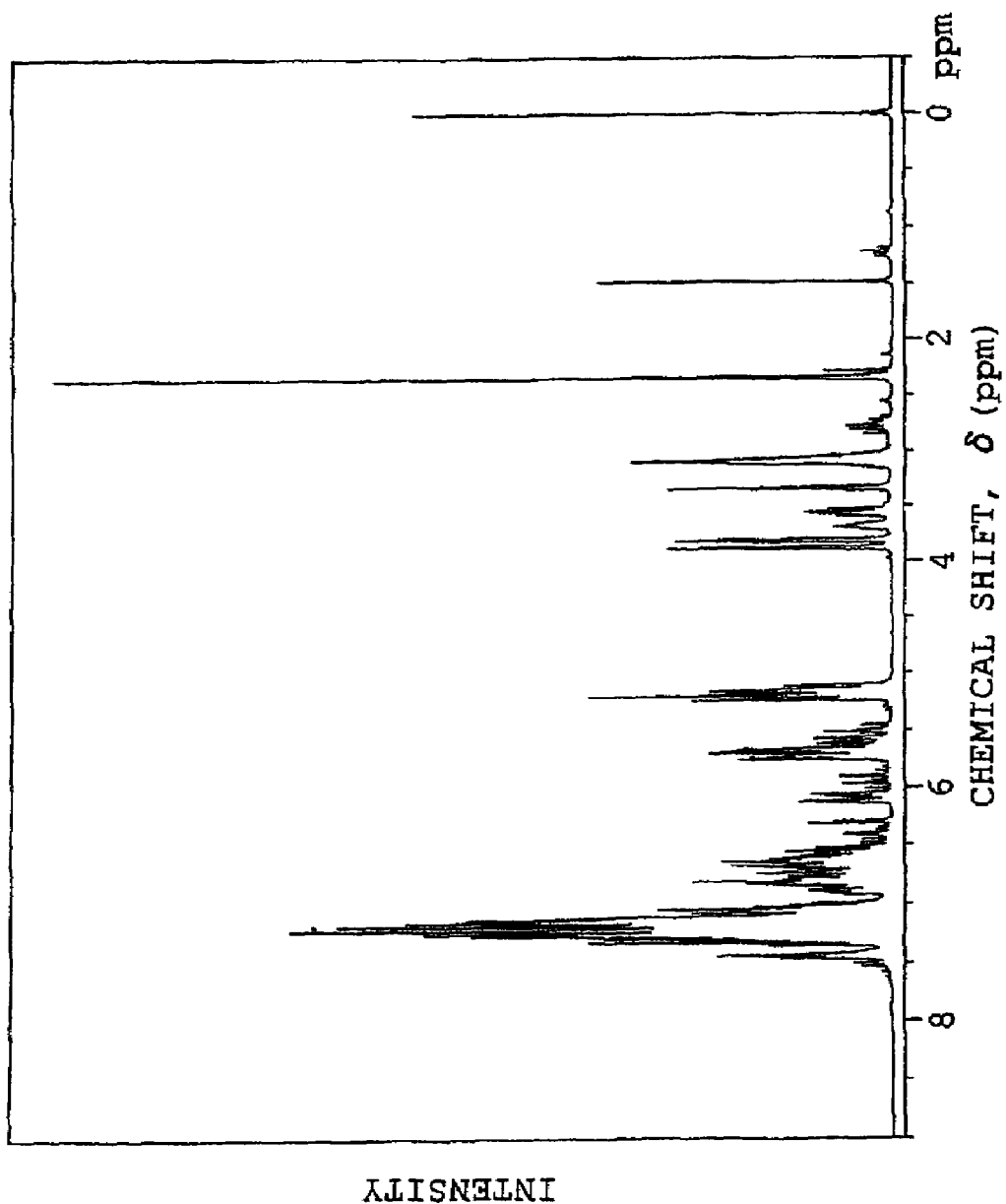
FIG. 8 shows the $^1$H-NMR spectrum of a compound 7 obtained in Example 10.
Figure 9:
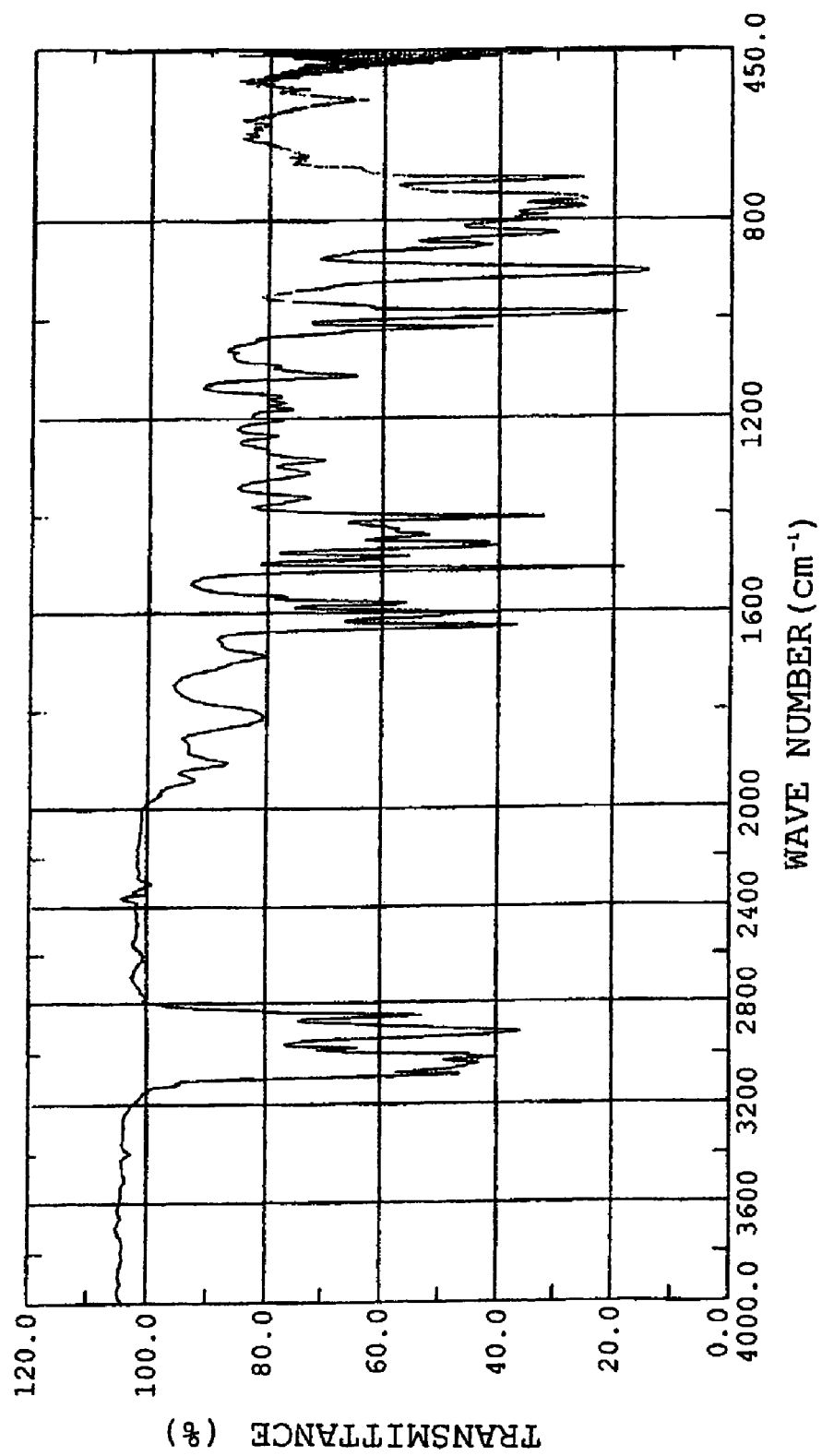
FIG. 9 shows the IR spectrum of a compound 7 obtained in Example 10.

Inside of a flask equipped with a thermoregulator, a stirrer, a cooling condenser, a dropping funnel, and a nitrogen inlet was replaced with nitrogen. 46.5 g (0.4 mol) of indene, 200 g of toluene, 7.75 g (0.024 mol) of tetra-n-butylammonium bromide, 0.08 g (0.0004 mol) of phenothiazine, and 128.0 g of a 50 wt % aqueous solution of NaOH (NaOH, 1.6 mol) were charged into the flask, and the mixture was heated to 50° C. under stirring, to thereby prepare a homogeneous solution. 134.1 g of vinylbenzyl chloride (CMS-AM; purity of 91%; 0.8 mol; m-/p-isomers: 50/50 wt % mixture; available from Seimi Chemical Co., Ltd.) was added dropwise to the dark blue green solution over 15 minutes, and a reaction was then carried out at 50 to 52° C. for 10 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a curable vinylbenzyl compound of the present invention (consisting of three compounds: a compound in which $R^3$, $R^4$, and $R^5$ each represent a vinylbenzyl group, and $R^6$ represents a hydrogen atom in the general formula 3; a compound in which two of $R^3$ to $R^5$ represent vinylbenzyl groups and the remaining represents a hydrogen atom, and $R^6$ represents a hydrogen atom in the general formula 3; and a compound in which one of $R^3$ to $R^5$ represents a vinylbenzyl group and the remaining represent hydrogen atoms, and $R^6$ represents a hydrogen atom in the general formula 3). The obtained compound is designated as Compound 7. Compound 7 was identified from its $^1$H-NMR spectrum, IR spectrum, and HPLC measurement. Compound 7 was a highly viscous liquid of about 5,000 poise at 23° C. FIG. 8 shows the $^1$H-NMR spectrum, and FIG. 9 shows the IR spectrum.

Compound 7 was poured between glass plates and was cured at 160° C. for 2 hours, at 180° C. for 2 hours, and then at 200° C. for 3 hours, to thereby form a resin plate having a thickness of 1.5 mm. Samples required for each measurement were prepared using the resin plate. Table 2 shows the results of the measurements.

EXAMPLE 11

Inside of a flask equipped with a thermoregulator, a stirrer, a cooling condenser, a dropping funnel, and a nitrogen inlet was replaced with nitrogen. 46.5 g (0.4 mol) of indene, 200 g of toluene, 3.88 g (0.012 mol) of tetra-n-butylammonium bromide, 0.04 g (0.0002 mol) of phenothiazine, and 64.0 g of a 50 wt % aqueous solution of NaOH (NaOH, 0.8 mol) were charged into the flask, and the mixture was heated to 50° C. under stirring, to thereby prepare a homogeneous solution. 80.4 g of vinylbenzyl chloride (CMS-AM; purity of 91%; 0.48 mol; m-/p-isomers: 50/50 wt % mixture; available from Seimi Chemical Co., Ltd.) was added dropwise to the dark blue green solution over 15 minutes, and a reaction was then carried out at 50 to 52° C. for 10 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a curable vinylbenzyl compound of the present invention (mainly composed of a compound in which one of $R^3$ to $R^5$ represents a vinylbenzyl group and the remaining represent hydrogen atoms, and $R^6$ represents a hydrogen atom in the general formula 3). The obtained compound is designated as Compound 8. Compound 8 was a viscous liquid of about 1,000 poise at 23° C. Compound 8 was identified from its $^1$H-NMR spectrum, IR spectrum, and HPLC measurement in the same manner as in Examples 9 and 10.

Compound 8 was poured between glass plates and was cured at 160° C. for 2 hours, at 180° C. for 2 hours, and then at 200° C. for 3 hours, to thereby form a resin plate having a thickness of 1.5 mm. Samples required for each measurement were prepared using the resin plate. Table 2 shows the results of the measurements.

EXAMPLE 12

Inside of a flask equipped with a thermoregulator, a stirrer, a cooling condenser, a dropping funnel, and a nitrogen inlet was replaced with nitrogen. 46.5 g (0.4 mol) of indene, 200 g of toluene, 3.88 g (0.012 mol) of tetra-n-butylammonium bromide, 0.04 g (0.0002 mol) of phenothiazine, and 64.0 g of a 50 wt % aqueous solution of NaOH (NaOH, 0.8 mol) were charged into the flask, and the mixture was heated to 50° C. under stirring, to thereby prepare a homogeneous solution. 67.0 g of vinylbenzyl chloride (CMS-AM; purity of 91%; 0.40 mol; m-/p-isomers: 50/50 wt % mixture; available from Seimi Chemical Co., Ltd.) was added dropwise to the dark blue green solution over 15 minutes, and a reaction was then carried out at 50 to 52° C. for 10 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a curable vinylbenzyl compound of the present invention (mainly composed of a compound in which one of $R^3$ to $R^5$ represents a vinylbenzyl group and the remaining represent hydrogen atoms, and $R^6$ represents a hydrogen atom in the general formula 3). The obtained compound is designated as Compound 9. Compound 9 was identified from its $^1$H-NMR spectrum, IR spectrum, and HPLC measurement in the same manner as in Examples 9 and 10.

Compound 9 was poured between glass plates and was cured at 160° C. for 2 hours, at 180° C. for 2 hours, and then at 200° C. for 3 hours, to thereby form a resin plate having a thickness of 1.5 mm. Samples required for each measurement were prepared using the resin plate. Table 2 shows the results of the measurements.

EXAMPLE 13

Figure 10:
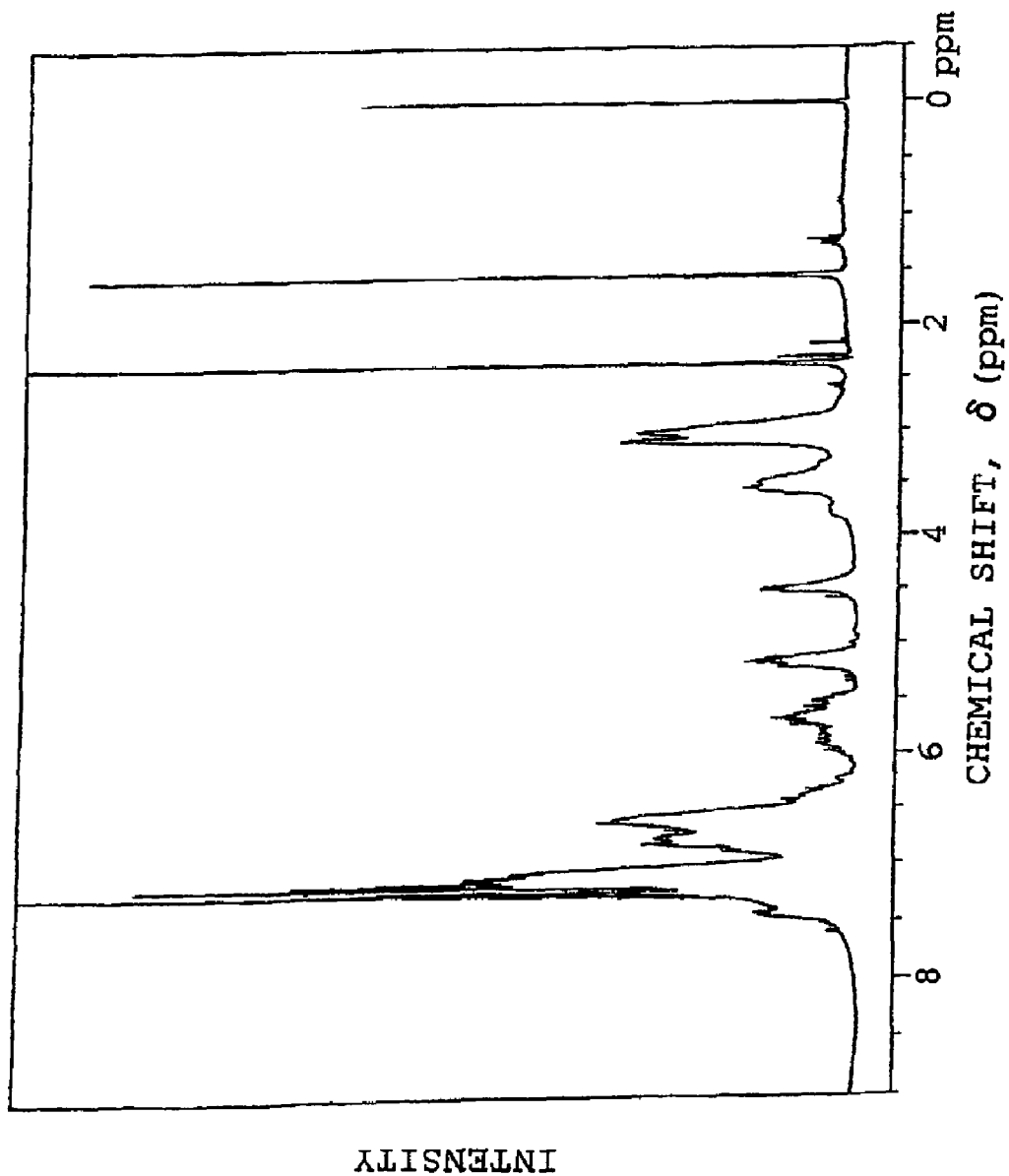
FIG. 10 shows the $^1$H-NMR spectrum of a compound 10 obtained in Example 13.
Figure 11:
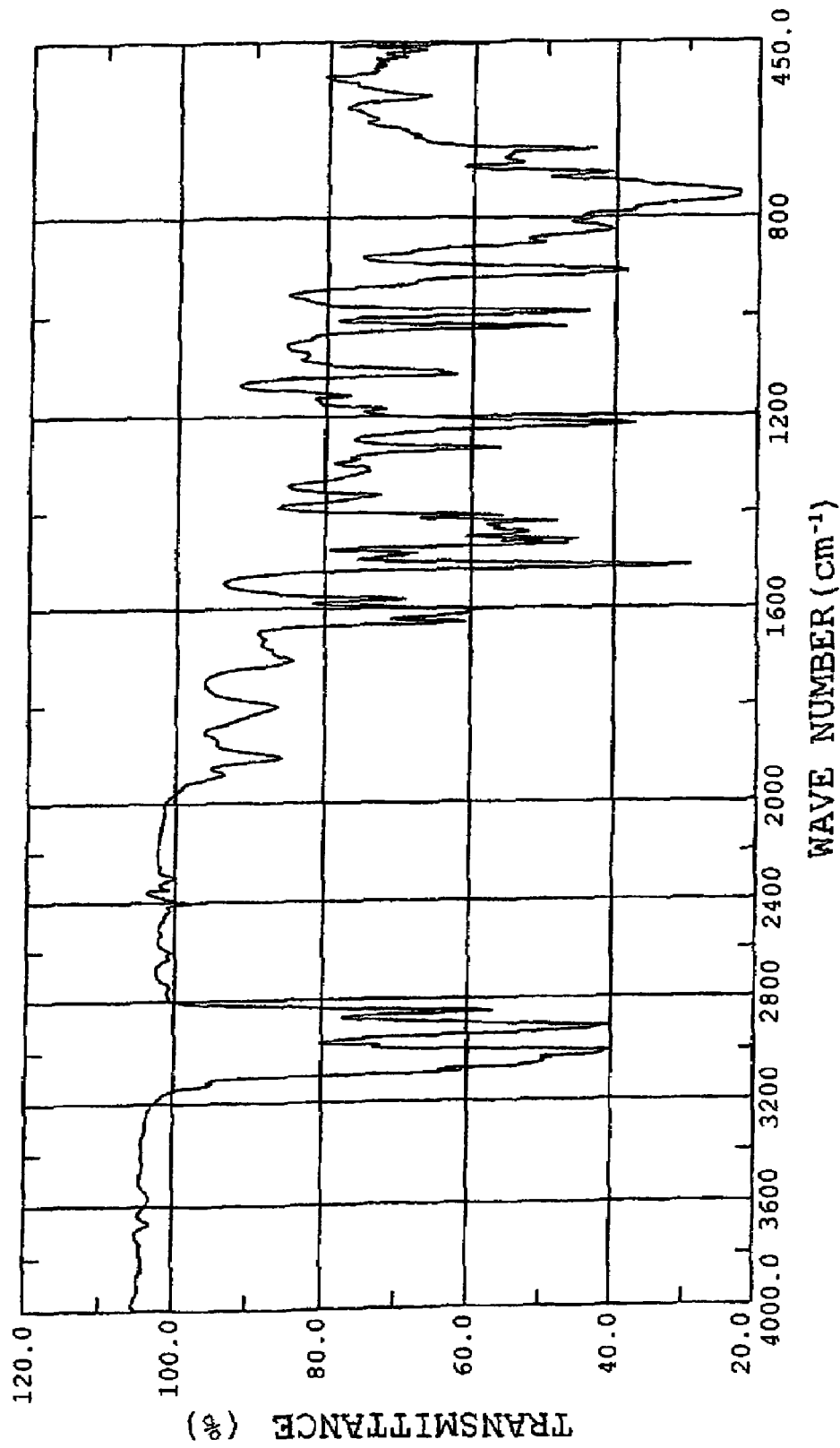
FIG. 11 shows the IR spectrum of a compound 10 obtained in Example 13.

166 g (1.43 mol) of indene, 1,000 g of toluene, 22 g (0.069 mol) of tetra-n-butylammonium bromide, 2.50 g (1.43 mol) of p-xylylene dichloride, and 240 g of vinylbenzyl chloride (CMS-AM; purity of 91%; 1.43 mol; m-/p-isomers: 50/50 wt % mixture; available from Seimi Chemical Co., Ltd.) were charged into a flask equipped with a thermoregulator, a stirrer, a cooling condenser, and a dropping funnel, and the mixture was heated to 40° C. under stirring, to thereby prepare a homogeneous solution. 344 g of a 50 wt % aqueous solution of NaOH (NaOH, 8.6 mol) was added to the solution, and a reaction was then carried out at 70° C. for 8 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a solid compound having a molecular weight Mw of 3,000 in which an oligomer compound containing indene connected by xylylene was substituted with a vinylbenzyl group (in which $R^6$ represents hydrogen, $R^7$ represents a xylylene group, $R^8$ represents a vinylbenzyl group, and a to c represent values providing an Mw of 3,000 in the general formula 4). The obtained compound is designated as Compound 10. Compound 10 was identified from its $^1$H-NMR spectrum. FIG. 10 shows the $^1$H-NMR spectrum of Compound 10 obtained in Example 13, and FIG. 9 shows the IR spectrum of Compound 10 obtained in Example 13.

Compound 10 was poured between glass plates and was cured at 160° C. for 2 hours, at 180° C. for 2 hours, and then at 200° C. for 3 hours, to thereby form a resin plate having a thickness of 1.5 mm. Samples required for each measurement were prepared using the resin plate. Table 2 shows the results of the measurements.

COMPARATIVE EXAMPLE 3

45 g (0.25 equivalent) of a dicyclopentadiene skeleton phenolic resin (DPP-3H, special phenolic resin, available from Nippon Petrochemicals Co., Ltd.), 38.1 g of vinylbenzyl chloride (CMS-AM; purity of 91%; 0.25 mol; m-/p-isomers: 50/50 wt % mixture; available from Seimi Chemical Co., Ltd.), 2.4 g of tetra-n-butylammonium bromide, 0.038 g of 2,4-dinitrophenol, and 200 g of methyl ethyl ketone were charged into a four-necked flask equipped with a thermoregulator, a stirrer, a cooling condenser, and a dropping funnel, and the mixture was dissolved under stirring. 40 g of a 50 wt % aqueous solution of NaOH (NaOH, 0.48 mol) was added dropwise at 75° C. to the obtained solution over 20 minutes, and a reaction was further carried out at 75° C. for 4 hours. The obtained mixture in the flask was neutralized with 2N hydrochloric acid, and 100 g of toluene was added. An organic layer was then washed with distilled water three times. After methyl ethyl ketone was distilled off under reduced pressure, a reaction product was precipitated in methanol to collect a solid matter through filtration, which was then dried at 50° C. in vacuum to obtain a vinylbenzyl ether compound. The obtained compound is designated as Compound 11.

Compound 11 was cured and molded into a resin plate in the same manner as in Example 9. Samples required for each measurement were prepared using the resin plate.

Table 2 shows the results of the measurements.

COMPARATIVE EXAMPLE 4

2 parts of 2-ethyl-4-methylimidazole (available from Shikoku Chemicals Corporation) was mixed with 100 parts of an epoxy resin (Epicoat 828, epoxy equivalent 188, available from Yuka-Shell Epoxy Co., Ltd.), to thereby prepare a resin composition. The obtained compound is designated as Compound 12.

Compound 12 was poured between glass plates and cured at 80° C. for 2 hours and then at 150° C. for 2 hours, to thereby form a resin plate. Samples required for each measurement were prepared using the resin plate. Table 2 shows the results of the measurements.

EXAMPLE 14

Figure 12:
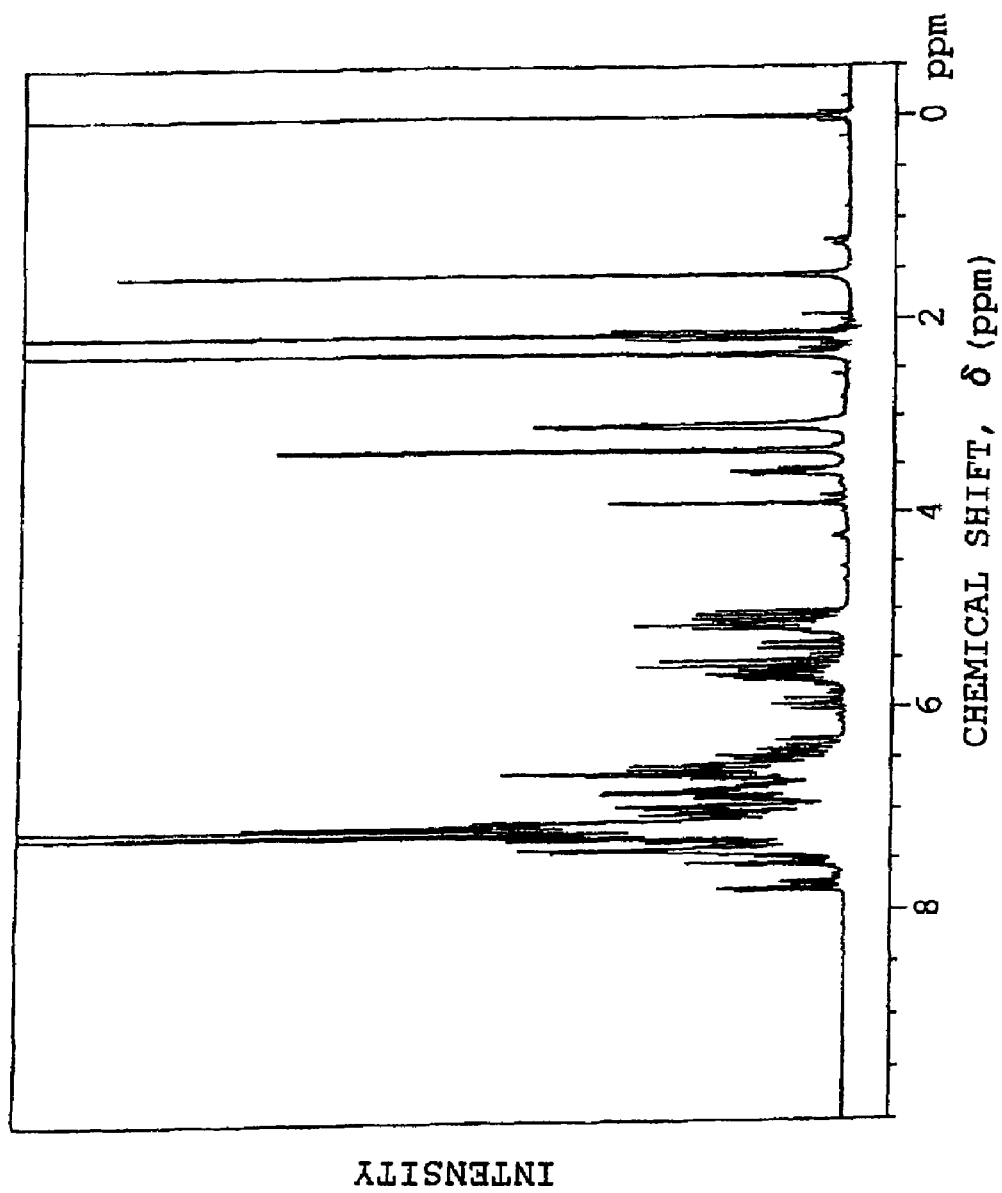
FIG. 12 shows the $^1$H-NMR spectrum of a compound 13 obtained in Example 14.

116 g (1 mol) of indene, 166 g (1 mol) of fluorene, 1,000 g of toluene, 22 g (0.069 mol) of tetra-n-butylammonium bromide, 70 g (0.4 mol) of p-xylylene dichloride, and 550 g of vinylbenzyl chloride (CMS-AM; purity of 91%; 3.6 mol; m-/p-isomers: 50/50 wt % mixture; available from Seimi Chemical Co., Ltd.) were charged into a flask equipped with a thermoregulator, a stirrer, a cooling condenser, and a dropping funnel, and the mixture was heated to 40° C. under stirring, to thereby prepare a homogeneous solution. 352 g of a 50 wt % aqueous solution of NaOH (NaOH, 8.8 mol) was added to the solution, and a reaction was then carried out at 70° C. for 8 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a solid compound having a molecular weight Mw of 700 in which an oligomer compound containing fluorene and indene connected by xylylene was substituted with a vinylbenzyl group. The obtained compound is designated as Compound 13. Compound 13 was identified from its $^1$H-NMR spectrum. FIG. 12 shows the $^1$H-NMR spectrum of Compound 13 obtained in Example 14.

Compound 13 was poured between glass plates and was cured at 160° C. for 2 hours, at 180° C. for 5 hours, and then at 200° C. for 3 hours, to thereby form a resin plate having a thickness of 1.5 mm. Samples required for each measurement were prepared using the resin plate. Table 3 shows the results of the measurements.

EXAMPLE 15

55 g (0.48 mol) of indene, 237 g (1.43 mol) of fluorene, 1,000 g of toluene, 22 g (0.069 mol) of tetra-n-butylammonium bromide, 250 g (1.43 mol) of p-xylylene dichloride, and 240 g of vinylbenzyl chloride (CMS-AM; purity of 91%; 1.43 mol; m-/p-isomers: 50/50 wt % mixture; available from Seimi Chemical Co., Ltd.) were charged into a flask equipped with a thermoregulator, a stirrer, a cooling condenser, and a dropping funnel, and the mixture was heated to 40° C. under stirring to prepare a homogeneous solution. 344 g of a 50 wt % aqueous solution of NaOH (NaOH, 8.6 mol) was added to the solution, and a reaction was then carried out at 70° C. for 8 hours. The obtained mixture in the flask was neutralized with 2N hydrochloric acid and washed with distilled water twice, and toluene was distilled off under reduced pressure. The obtained orange viscous liquid was washed with metha-

TABLE 2

Figure 13:
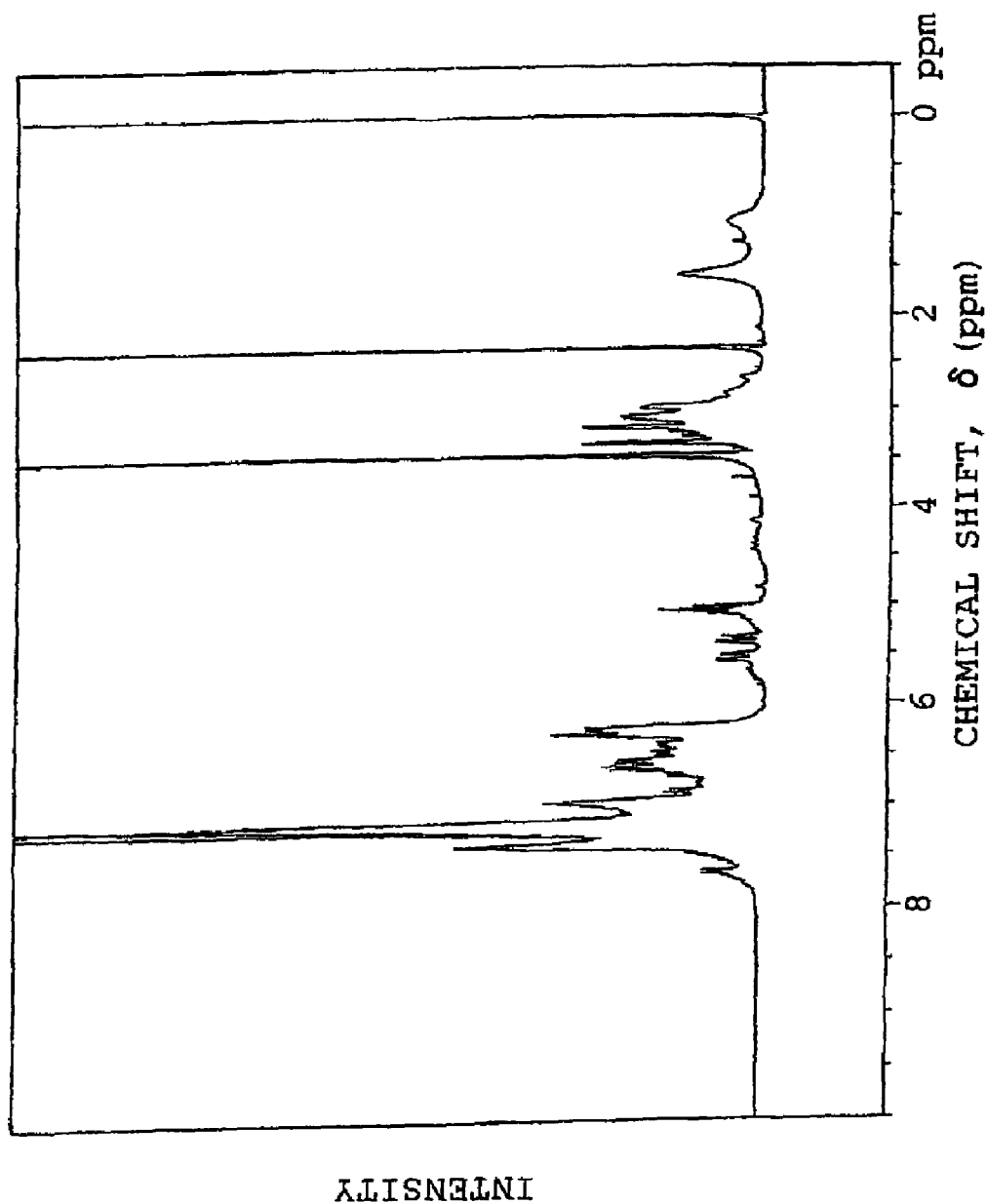
FIG. 13 shows the $^1$H-NMR spectrum of a compound 14 obtained in Example 15.

| Cured product physical properties | Example 9 | Example 10 | Example 11 | Example 12 | Example 13 | Comparative Example 3 | Comparative Example 4 |
|---|---|---|---|---|---|---|---|
| Dielectric constant (5 GHz) | 2.66 | 2.65 | 2.70 | 2.71 | 2.63 | 2.85 | 3.25 |
| Dielectric dissipation factor (5 GHz) | 0.0018 | 0.0019 | 0.0015 | 0.0013 | 0.0041 | 0.0075 | 0.0253 |
| 5% weight reduction temperature (° C.) | 410 | 400 | 383 | 377 | 385 | 371 | 399 |
| Water absorption (%) | 0.065 | 0.050 | 0.052 | 0.060 | 0.070 | 0.157 | 1.389 | nol and then dried in vacuum, to thereby obtain a solid compound having a molecular weight Mw of 3,000 in which an oligomer compound containing fluorene and indene connected by xylylene was substituted with a vinylbenzyl group. The obtained compound is designated as Compound 14. Compound 14 was identified from its $^1$H-NMR spectrum. FIG. 13 shows the $^1$H-NMR spectrum of Compound 14 obtained in Example 15.

Compound 14 was poured between glass plates and was cured at 160° C. for 2 hours, af 180° C. for 5 hours, and then at 200° C. for 3 hours, to thereby form a resin plate having a thickness of 1.5 mm. Samples required for each measurement were prepared using the resin plate. Table 3 shows the results of the measurements.

REFERENCE EXAMPLE 1

49.8 g (0.3 mol) of fluorene, 220 g of toluene, 2.91 g ($9 \times 10^{-3}$ mol) of tetra-n-butylammonium bromide, and 96 g of a 50 wt % aqueous solution of NaOH (purity of 95%, 1.14 mol) were charged into a 1-liter four-necked flask equipped with a thermoregulator, a stirrer, a cooling condenser, and a dropping funnel, and the mixture was heated to 65° C. 21 g (0.12 mol) of p-xylylene dichloride was added, and a reaction was carried out for 2.5 hours. After results of the $^1$H-NMR measurement of a small amount of the reaction product confirmed that p-xylylene dichloride was consumed, 54 g of CMS-AM (purity of 91%; 0.36 mol) was added dropwise to the reaction system, and the reaction was continued at 65° C. for 6.5 hours. After the reaction liquid was cooled to room temperature, 2N hydrochloric acid was added to neutralize the reaction mixture. An organic layer was washed with distilled water three times. After the solvent was distilled off under reduced pressure, the obtained solid was pulverized in methanol and filtered to collect a solid matter through filtration. The solid matter was then dried at 50° C. in a vacuum oven, to thereby obtain an oligomer compound containing fluorene connected by xylylene. The obtained compound is designated as Compound 15.

Compound 15 was poured between glass plates and was cured at 160° C. for 2 hours, at 180° C. for 5 hours, and then at 200° C. for 3 hours, to thereby form a resin plate having a thickness of 1.5 mm. Samples required for each measurement were prepared using the resin plate. Table 3 shows the results of the measurements.

REFERENCE EXAMPLE 2

Equal amounts of Compound 10 and Compound 15 were mixed, and the mixture was poured between glass plates and was cured at 160° C. for 2 hours, at 180° C. for 5 hours, and then at 200° C. for 3 hours, to thereby form a resin plate having a thickness of 1.5 mm. Samples required for each measurement were prepared using the resin plate. Table 3 shows the results of the measurements.

TABLE 3

| Cured product physical properties | Example 14 | Example 15 | Reference Example 1 | Reference Example 2 |
| --- | --- | --- | --- | --- |
| Dielectric constant (5 GHz) | 2.66 | 2.63 | 2.70 | 2.65 |
| Dielectric dissipation factor (5 GHz) | 0.0031 | 0.0038 | 0.0028 | 0.0038 |
| 5% weight reduction temperature (° C.) | 405 | 411 | 364 | 376 |
| Water absorption (%) | 0.065 | 0.070 | 0.110 | 0.080 |

Further, the high-frequency substrate of the present invention will be described, but the present invention is not limited to examples below. The measurement methods carried out in Examples 16 to 19 and Comparative Examples 5 and 6 are shown below.

Dielectric properties: A dielectric constant and a dielectric dissipation factor at 5 GHz of a prism sample of 1.6 mm×1.5 mm×75 mm were measured using a vector network analyzer HP8753E available from Hewlett-Packard Japan, Ltd. in accordance with a cavity resonator perturbation method.

$^1$H-nuclear magnetic resonance spectrum ($^1$H-NMR): measured using tetramethylsilane as an internal standard material and JNM-LA300 available from JEOL Ltd.

Gel permeation chromatography (GPC): measured using Shodex GPC System-21 (columns KF-802, KF-803, KF-805) available from SHOWA DENKO K.K. at an elution rate of 1 ml/minute using tetrahydrofuran as an elute. The GPC was adopted for molecular weight determination.

Solder heat resistance test: carried out in accordance with JIS C 0054 by immersing a sample in a solder bath at 260° C. for 120 seconds to check if there were any changes in a surface state or shape of the sample.

EXAMPLE 16

249 g (1.5 mol) of fluorene, 250 g of toluene, 22 g (0.069 mol) of tetra-n-butylammonium bromide, 76 g (1.0 mol) of allyl chloride, and 335 g of vinylbenzyl chloride (CMS-AM; purity of 91%; 2.0 mol; m-/p-isomers: 50/50 wt % mixture; available from Seimi Chemical Co., Ltd.) were charged into a flask equipped with a thermoregulator, a stirrer, a cooling condenser, a dropping funnel, and an oxygen inlet, and the mixture was heated to 40° C. under stirring, to thereby prepare a homogeneous solution. 240 g of a 50 wt % aqueous solution of NaOH (NaOH, 6 mol) was added to the solution, and a reaction was then carried out at 60° C. for 8 hours. The obtained mixture in the flask was neutralized with 2N hydrochloric acid and washed with distilled water twice, and toluene was distilled off under reduced pressure. The obtained orange viscous liquid was dried in vacuum, to thereby obtain a semi-solid compound containing fluorene substituted with a vinylbenzyl group and an allyl group. The obtained compound is designated as Compound 16. Compound 16 was identified from its $^1$H-NMR spectrum.

Next, a glass cloth (WEA18K105BZ2, available from Nitto Boseki Co., Ltd.) was impregnated with a 60% toluene solution of Compound 16, and the whole was dried at 120° C. for 60 minutes, to thereby obtain a prepreg. A 10-ply prepreg laminate was prepared and molded under heat and pressure (40 kg/cm$^2$) at 150° C. for 2 hours, at 180° C. for 5 hours, and at 200° C. for 5 hours, to thereby obtain a laminated plate having a thickness of 1.6 mm and a glass fiber content of 60%.

EXAMPLE 17

Inside of a flask equipped with a thermoregulator, a stirrer, a cooling condenser, a dropping funnel, and a nitrogen inlet was replaced with nitrogen. 46.5 g (0.4 mol) of indene, 200 g of toluene, 7.75 g (0.024 mol) of tetra-n-butylammonium bromide, 0.08 g (0.0004 mol) of phenothiazine, and 128.0 g of a 50 wt % aqueous solution of NaOH (NaOH, 1.6 mol) were charged into the flask, and the mixture was heated to 50° C. under stirring to prepare a homogeneous solution. 34.1 g of vinylbenzyl chloride (CMS-AM; purity of 91%; 0.8 mol; m-/p-isomers: 50/50 wt % mixture; available from Seimi Chemical Co., Ltd.) was added dropwise to the dark blue green solution over 15 minutes, and a reaction was then carried out at 50 to 52° C. for 10 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a liquid compound containing indene substituted with a vinylbenzyl group. The obtained compound is designated as Compound 17. Compound 17 was identified from its $^1$H-NMR spectrum.

Next, a glass cloth (WEA 18K105BZ2, available from Nitto Boseki Co., Ltd.) was impregnated with Compound 17, and the whole was dried at 120° C. for 30 minutes, to thereby obtain a prepreg. A 10-ply prepreg laminate was prepared and molded under heat and pressure (40 kg/cm$^2$) at 150° C. for 2 hours and at 180° C. for 6 hours, to thereby to obtain a laminated plate having a thickness of 1.6 mm and a glass fiber content of 62%.

EXAMPLE 18

55 g (0.48 mol) of indene, 237 g (1.43 mol) of fluorene, 1,000 g of toluene, 22 g (0.069 mol) of tetra-n-butylammonium bromide, 250 g (1.43 mol) of p-xylylene dichloride, and 240 g of vinylbenzyl chloride (CMS-AM; purity of 91%; 1.43 mol; m-/p-isomers: 50/50 wt % mixture; available from Seimi Chemical Co., Ltd.) were charged into a flask equipped with a thermoregulator, a stirrer, a cooling condenser, and a dropping funnel, and the mixture was heated to 40° C. under stirring, to thereby prepare a homogeneous solution. 344 g of a 50 wt % aqueous solution of NaOH (NaOH, 8.6 mol) was added to the solution, and a reaction was then carried out at 70° C. for 8 hours. The obtained mixture in the flask was neutralized with 2N hydrochloric acid and washed with distilled water twice, and toluene was distilled off under reduced pressure. The obtained orange viscous liquid was washed with methanol and then dried in vacuum, to thereby obtain a solid compound having a weight average molecular weight Mw of 3,000 in which an oligomer compound containing fluorene and indene connected by xylylene was substituted with a vinylbenzyl group. The obtained compound is designated as Compound 18. Compound 18 was identified from its $^1$H-NMR spectrum.

Next, a glass cloth (WEA18K105BZ2, available from Nitto Boseki Co., Ltd.) was impregnated with a 60% toluene solution of Compound 18, and the whole was dried at 120° C. for 60 minutes, to thereby obtain a prepreg. A 10-ply prepreg laminate was prepared and molded under heat and pressure (40 kg/cm 2) at 150° C. for 2 hours and at 180° C. for 6 hours, to thereby obtain a laminated plate having a thickness of 1.6 mm and a glass fiber content of 60%.

EXAMPLE 19

A glass cloth (WEA18K105BZ2, available from Nitto Boseki Co., Ltd.) was impregnated with a 60% toluene solution prepared by adding 10 parts of phenyl maleimide with respect to 90 parts of Compound 16 obtained in Example 16, and the whole was dried at 120° C. for 60 minutes, to thereby obtain a prepreg. A 10-ply prepreg laminate was prepared and molded under heat and pressure (40 kg/cm 2) at 150° C. for 2 hours, at 180° C. for 5 hours, and at 200° C. for 5 hours, to thereby obtain a laminated plate having a thickness of 1.6 mm and a glass fiber content of 61%.

EXAMPLE 20

A resin solution prepared by dissolving 100 parts of Compound 16 obtained in Example 16 and 120 parts of Compound 17 obtained in Example 17 in 80 parts of toluene was applied to a 35 μm-thick copper foil (3EC, available from Mitsui Mining & Smelting Co., Ltd.) to a thickness of 100 μm. The whole was dried at 100° C. for 60 minutes and heated at 120° C. for 2 hours, to thereby obtain a semi-cured product (two products were produced). The two copper foils each having a resin were piled in such a manner that the resins were brought into contact with each other and were molded under heat and pressure (40 kg/cm$^2$) at 150° C. for 2 hours and at 180° C. for 6 hours, to thereby obtain a sample. Peel strength of the copper foil measured in accordance with JIS C 6481 using the sample was 1.2 kgf/cm.

COMPARATIVE EXAMPLE 5

45 g (0.25 equivalent) of a dicyclopentadiene skeleton phenolic resin (DPP-3H, special phenolic resin, available from Nippon Petrochemical Co., Ltd.), 38.1 g of vinylbenzyl chloride (CMS-AM; purity of 91%; 0.25 mol; m-/p-isomers: 50/50 wt % mixture; available from Seimi Chemical Co., Ltd.), 2.4 g of tetra-n-butylammonium bromide, 0.038 g of 2,4-dinitrophenol, and 200 g of methyl ethyl ketone were charged into a 1-liter four-necked flask equipped with a thermoregulator, a stirrer, a cooling condenser, and a dropping funnel and dissolved under stirring. 40 g of a 50 wt % aqueous solution of NaOH (NaOH purity of 95%, 0.475 mol) was added dropwise at 75° C. to the obtained solution over 20 minutes, and the whole was stirred at 75° C. for additional 4 hours. After the obtained reaction mixture was cooled to room temperature, the mixture was neutralized with 2N hydrochloric acid, and 100 g of toluene was added. An organic layer was then washed with 300 g of distilled water three times. After methyl ethyl ketone was removed under reduced pressure, a reaction product was precipitated in 300 ml of methanol to collect a solid matter through filtration, which was then dried at 50° C. in a vacuum oven to obtain a vinylbenzyl ether compound at an yield of 95%. The obtained compound is designated as Compound 19.

Next, a glass cloth (WEA18K105BZ2, available from Nitto Boseki Co., Ltd.) was impregnated with a resin solution prepared by dissolving Compound 19 in a 60% toluene solution, and the whole was dried at 120° C. for 90 minutes, to thereby obtain a prepreg. A 10-ply prepreg laminate was prepared and molded under heat and pressure (40 kg/cm$^2$) at 150° C. for 2 hours and at 180° C. for 6 hours, to thereby to obtain a laminated plate having a thickness of 1.6 mm and a glass fiber content of 62%.

COMPARATIVE EXAMPLE 6

A resin solution was prepared by dissolving 90 parts of a bisphenol A-type epoxy resin (Epicoat 1001, available from Japan Epoxy Resins Co., Ltd.), 10 parts of a novolak-type epoxy resin (DEN 438, available from Dow Chemical Japan Ltd.), 5 parts of dicyandiamide as a curing agent, and 0.3 part of benzyldimethylamine as a curing accelerator in 70 parts of acetone. A glass cloth (WEA18K105BZ2, available from Nitto Boseki Co., Ltd.) was impregnated with the resin solution, and the whole was dried at 80° C. for 5 minutes and at 160° C. for 5 minutes, to thereby obtain a prepreg. A 10-ply prepreg laminate was prepared and molded under heat and pressure (70 kg/cm$^2$) at 160° C. for 1 hour, to thereby to obtain a laminated plate having a thickness of 1.6 mm and a glass fiber content of 62%.

Table 4 shows the physical properties of the laminated plates obtained in Examples 16 to 19 and Comparative Examples 5 and 6.

TABLE 4

| Laminated plate physical properties | Example 16 | Example 17 | Example 18 | Example 19 | Comparative Example 5 | Comparative Example 6 |
|---|---|---|---|---|---|---|
| Dielectric constant (5 GHz) | 4.0 | 4.1 | 3.9 | 4.1 | 4.1 | 4.5 |
| Dielectric dissipation factor (5 GHz) | 0.0035 | 0.0040 | 0.0050 | 0.0030 | 0.01 | 0.02 |
| Solder heat resistance (260° C.) | 120 sec. or more | 120 sec. or more | 120 sec. or more | 120 sec. or more | 120 sec. or more | 120 sec. or more |

INDUSTRIAL APPLICABILITY

According to the present invention, there is provided a polyvinyl benzyl compound which provides a cured product having high heat resistance, low water absorption, a low dielectric constant and a low dielectric dissipation factor, a process for producing the polyvinyl benzyl compound, a curable resin composition comprising the polyvinyl benzyl compound, and a cured resin obtained by curing the composition.

Further, according to the present invention, there are provided a substrate, a prepreg, and a metal foil having a resin all of which have excellent dielectric properties at a high frequency range, in particular, a low dielectric dissipation factor, and high heat resistance.

What is claimed is:

1. A curable polyvinyl benzyl compound represented by the following general formula 1:

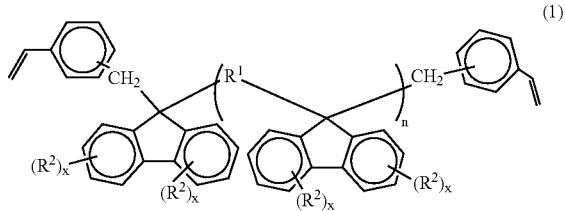

(wherein $R^1$ is a divalent organic group having 2 to 20 carbon atoms, $R^2$ is at least one organic group selected from the group consisting of a hydrogen atom, a halogen atom, an alkyl group, an alkoxy group and a thioalkoxy group having 1 to 5 carbon atoms, which may be the same or different, and an aryl group, where x is an integer of 0 to 4, and n is an integer of 1 to 20).

2. A curable resin composition prepared by mixing a curable polyvinyl benzyl compound according to claim 1 with a monomer, an oligomer and/or a polymer which is copolymerizable with said compound.

3. A cured resin obtained by curing a curable polyvinyl benzyl compound according to claim 1.

4. A cured resin obtained by curing a curable resin composition according to claim 2.

5. A high-frequency substrate obtained by curing a curable polyvinyl benzyl compound according to claim 1.

6. A high-frequency substrate obtained by curing a curable resin composition according to claim 2.

7. A prepreg obtained by impregnating a curable resin composition according to claim 2 with a fiber material.

8. A high-frequency substrate obtained by heating and pressurizing either a single prepreg according to claim 7 or a laminate of the prepregs according to claim 7.

9. A metal-lined high-frequency substrate obtained by placing a metal foil onto either a single prepreg according to claim 7 or a laminate of the prepregs according to claim 7, through heating and pressurizing.

10. A metal foil having a resin obtained by applying a curable resin composition according to claim 2 to a metal foil to be integrated.

11. A multi-layer laminate substrate characterized by having a curable resin composition according to claim 2 applied to a conductive layer, which is polymerized and cured, and a conductive layer formed on a cured product.

* * * * *